US012791545B2

(12) United States Patent
Di Santo et al.

(10) Patent No.: US 12,791,545 B2
(45) Date of Patent: Nov. 10, 2026

(54) DIAGENESIS PREDICTION BASED ON THIN SECTION IMAGE ANALYSIS AND OPEN-HOLE LOGS

(71) Applicant: Saudi Arabian Oil Company, Dhahran (SA)

(72) Inventors: Simone Di Santo, Dammam (SA); Hakima Ali Lahmar, Virginia Water (GB); Sachit Saumya, Issy-les-Moulineaux (FR); Mohammed A. Masrahy, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 294 days.

(21) Appl. No.: 18/764,794

(22) Filed: Jul. 5, 2024

(65) Prior Publication Data

US 2026/0009779 A1 Jan. 8, 2026

(51) Int. Cl.
*G01N 33/24* (2006.01)
*G06T 7/00* (2017.01)

(52) U.S. Cl.
CPC ......... *G01N 33/241* (2013.01); *G06T 7/0004* (2013.01); *G06T 2207/20081* (2013.01)

(58) Field of Classification Search
CPC ................ G01N 33/241; G06T 7/0004; G06T 2207/20081; G01V 20/00
See application file for complete search history.

(56) References Cited

U.S. PATENT DOCUMENTS 11,873,709 B2 1/2024 Wang et al.
2020/0132657 A1* 4/2020 King, Jr. ................ G01N 33/24
2021/0270130 A1* 9/2021 Lu ........................... E21B 44/00
2023/0304391 A1* 9/2023 Sheng ..................... E21B 25/00

FOREIGN PATENT DOCUMENTS

WO WO-2020225592 A1 * 11/2020 ......... G06F 18/2413

OTHER PUBLICATIONS

International Search Report and Written Opinion in International Appln. No. PCT/US2025/036096, mailed on Nov. 4, 2025, 15 pages.
Jin et al., "Review of diagenetic facies in tight sandstones: Diagenesis, diagenetic minerals, and prediction via well logs," Earth-Science Reviews, Jun. 2018, 185:234-258, 25 pages.
(Continued)

*Primary Examiner* — Thomas M Hammond, III
(74) *Attorney, Agent, or Firm* — Fish & Richardson P.C.

(57) ABSTRACT

Systems and methods for determining a diagenesis level in a reservoir for performing hydrocarbon extraction include receiving a set of open hole (OH) log data from one or more wells in the reservoir, the OH log data representing a subsurface of the reservoir; executing a diagenesis model to process the set of OH log data, the diagenesis model trained by thin-section image data correlated to labeled OH log data, the labeling identifying values for a quartz overgrowth rate (QOR), a clay coating rate (CCR), or a thin-section porosity in the subsurface based on a value in the OH log data; determining a prediction of a porosity of the reservoir, a permeability of the reservoir, or both the porosity and the permeability; and generating a control signal representing a recommendation to drill a well at a location in the reservoir.

20 Claims, 11 Drawing Sheets

(56) References Cited

OTHER PUBLICATIONS

Sherif et al., "Characterization of the Gas-Bearing Tight Paleozoic Sandstone Reservoirs of the Risha Field, Jordan: Inferences on Reservoir Quality and Productivity," Arabian Journal for Science and Engineering, Apr. 2024, 50:215-235, 44 pages.

Worden et al., "Chlorite in sandstones," Earth-Science Reviews, Jan. 2020, 204:234-255, 38 pages.

Andaru et al., "Deep Learning to Infer Geothermal Reservoir Quality from Scanning Electron Microscope (SEM) Images," Proceedings, 49th Workshop on Geothermal Reservoir Engineering, Feb. 12-14, 2024, 11 pages.

Lai et al., "Review of diagenetic facies in tight sandstones: Diagenesis, diagenetic minerals, and prediction via well logs," Earth-Science Reviews, 2018, 185:234-254, 25 pages.

Verma et al., "Chapter 16—Imaging and interpretation: Seismic, rock physics and image log analysis workflows for deepwater systems," Deepwater Sedimentary Systems, 2022, pp. 555-591, 37 pages.

Wooldridge et al., "How to Quantify Clay-Coat Grain Coverage in Modern and Ancient Sediments," Journal of Sedimentary Research, Feb. 2019, 89:135-146, 12 pages.

* cited by examiner

DIAGENESIS PREDICTION BASED ON THIN SECTION IMAGE ANALYSIS AND OPEN-HOLE LOGS

TECHNICAL FIELD

The present disclosure relates to wellbore drilling, such as for hydrocarbon extraction. More specifically, the disclosure describes techniques for estimating reservoir quality at locations in the reservoir by predicting a diagenesis level at those locations in the reservoir.

BACKGROUND

Diagenesis collectively refers to physical, chemical, and biological changes which may occur during the formation of sedimentary rocks. Specifically, diagenesis refers to physical and/or chemical processes that affect sedimentary materials after deposition and before metamorphism and between deposition and weathering. Recrystallization, compaction, cementation, and lithification are all examples of diagenetic changes. Diagenesis has been divided, based on hydrocarbon and coal genesis into three phases including eodiagenesis, mesodiagenesis, and telodiagenesis. During the early or eodiagenesis stage shales lose pore water, little to no hydrocarbons are formed, and coal varies between lignite and sub-bituminous. During mesodiagenesis, dehydration of clay minerals occurs, the main development of oil genesis occurs, and high to low volatile bituminous coals are formed. During telodiagenesis, organic matter undergoes cracking and dry gas is produced. Additionally, semi-anthracite coals develop. The effects of diagenetic processes on rock properties such as porosity and the degree of lithification are progressive.

SUMMARY

Diagenesis can be challenging to investigate and predict. However, diagenesis can have a significant effect on reservoir quality and influence well placement for hydrocarbon extraction. Diagenesis analysis is typically based on analysis of thin-section images and core laboratory studies. The systems and methods described herein are configured for quantitatively characterizing a diagenesis level of continental deposits based on associated well logs and thin sections data. The systems and methods described herein can focuses on two types of diagenesis that impact an initial formation's porosity and permeability values. The two types of diagenesis can include quartz overgrowth analysis and clay coating analysis.

The data processing system is configured to analyze thin section images data automatically. The data processing system extracts values for relevant quantitative parameters including the quartz overgrowth rate and clay coating rate. The data processing system uses the values of these parameters to label a set of open-hole logs with the implementation of a machine learning model. The model will therefore predict Quartz Overgrowth Rate (QOR) and Clay Coating Rate (CCR) using the defined open hole logs set as input.

The data processing system uses the thin sections images data for diagenesis analysis. In some implementations, the data processing system automatically performs aspects of diagenesis analysis such as porosity measurements and grain size analysis. The data processing system is configured to incorporate this analysis in a decisional process for estimation of reservoir quality. Reservoir quality refers to a set of rock characteristics or parameters that characterize storage, distribution, and flow of fluids occur within the reservoir. The data processing system is configured to estimate values of these parameters and estimate or extrapolate values for these parameters to different locations within a given reservoir volume.

The data processing system and methods described herein correlate petrographic thin section analysis and analysis of well-logs of a reservoir. The systems and methods described herein are configured to predict quartz overgrowth and clay coating values and generation of synthetic log data.

Generally, the data processing system is configured for a clastic reservoir with minimal or absent chemical-precipitation related depositional environment (such as evaporites and carbonates). Generally, the data processing system does not focus on geothermal or hydrothermal facies and related medium-high temperature mineral alteration, but rather feldspars and clay alteration and mineral neo-genesis.

The data processing system performs the following general actions for estimation of reservoir quality. The data processing system generates models of reservoir quality-related diagenesis including at least quartz overgrowth (QO) and clay coating (CC) analysis. The data processing system processes data from open-hole logs and applies a diagenesis model for the prediction that is focused on particular locations or regions within a given reservoir.

The data processing system is configured to perform thin-section parameters extraction. The data processing system performs an overlapping open hole log labeling and diagenesis model generation. The data processing system applies the generated diagenesis model to predict values for QO and CC parameters and estimate reservoir quality.

The one or more embodiments described in this specification can enable one or more of the following advantages.

The data processing system uses the values of the diagenesis parameters quartz overgrowth ratio (QOR), clay coating ratio (CCR), and thin-section porosity (TSP) values to generate an estimate of a reservoir quality at various locations in the reservoir. Reservoir quality is related to the determined values of QOR, CCR, and TSP. Specifically, reservoir quality represents an ability of a reservoir to store fluid and/or allow fluid flow. Porosity and permeability are amongst the main parameters reprinting reservoir quality, with higher porosity and higher permeability usually correlating to higher reservoir quality. Clay coating and quartz overgrowth, or a combination thereof, have a direct impact on both permeability and porosity. Quartz overgrowth can obliterate porosity, reduce pore connection, and increase the flow tortuosity, reducing the subsurface permeability. Clay coating reduces the pore volume and reduce or obstruct the pore having a direct impact on porosity and permeability as well.

The data processing system can cause or control both improved well placement and well drilling, relative to well placement and drilling based on prior machine learning models or other approaches to diagenesis analysis. The improved placement of wells can result in a greater chance of successful production from the drilled wells. The data processing system can determine or predict reservoir quality in areas where log data are not directly available by extrapolating reservoir diagenesis to new regions of the reservoir. For example, the data processing system is configured to propagate the QO and CC rates along the locations represented in the logs where no thin-sections data are available. The data processing system generates a volumetric model at locations in the reservoir where no log data or thin-sections data are available. The data processing system generates the volumetric model based on values of the logs and values representing reservoir geometry including seismic data, reservoir structure data, sedimentary bodies data, and so forth. The data processing system, based on the volumetric model, can recommend well placement for improved well production. The data processing system can generate an improved dynamic reservoir model representing or predicting how fluid flow will evolve in the reservoir over time (e.g., history-matching analysis for the reservoir).

Embodiments of these systems and methods can include one or more of the following features.

In a general aspect, a method for determining a diagenesis level in a reservoir for performing hydrocarbon extraction includes receiving a set of open hole (OH) log data from one or more wells in the reservoir, the OH log data representing a subsurface of the reservoir; executing a diagenesis model to process the set of OH log data, the diagenesis model being trained by thin-section image data that are correlated to labeled OH log data, the labeling identifying values for a quartz overgrowth rate (QOR), a clay coating rate (CCR), or a thin-section porosity in the subsurface based on a value in the OH log data and a type of the OH log; determining, based on the executing, a prediction of a porosity of the reservoir, a permeability of the reservoir, or both the porosity and the permeability; and generating, based on the predicted porosity, a control signal representing a recommendation to drill a well at a location in the reservoir.

In some implementations, the process includes based on the predicted diagenesis level in the reservoir, generating a control signal configured for causing drilling of a well in the reservoir corresponding to a location a higher values of QOR, CCR, or VP relative to another location in the reservoir.

In some implementations, the diagenesis model is trained by performing operations comprising: obtaining image data from an imaging device, the image data representing at least a portion of a subsurface of the reservoir; obtaining at least one thin-section image from the image data; segmenting the thin-section image into a set of segments, each segment of the set including at least one grain; extracting, from a segment of the set, first data representing a first ratio of quartz overgrowth particles to total particles; extracting, from the segment of the set, second data representing a second ratio of a clay coated perimeter value to a total perimeter value; and training the diagenesis model based on the first ratio and the second ratio to predict the diagenesis level in the subsurface of the reservoir.

In some implementations, the process includes determining a visual porosity value for the portion of the subsurface of the reservoir by: extracting region color data from the segment of the set; filtering the segment of the set to remove blue color data from the segment; extracting a region size data from the segment of the set based on the filtering; determining a region size distribution based on the region size data; and determining a third ratio of the visual porosity area to a total area, wherein the third ratio represents a thin-section porosity value, and wherein a reservoir quality is based on the thin-section porosity value.

In some implementations, the OH log data comprises one or more of a thorium concentration log, a potassium concentration log, a shear slowness log, and a photoelectric absorption properties log.

In some implementations, the OH log data comprises one or more of a thorium concentration log, a potassium concentration log, a sonic shear slowness log, a sonic compressional slowness log, and/or a density log.

In some implementations, the OH log data comprises one or more of a sonic shear slowness log, a sonic compressional slowness log, a nuclear magnetic resonance (NMR) log, a dielectric log, and a density log.

The previously described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method, the instructions stored on the non-transitory, computer-readable medium.

The details of one or more embodiments are set forth in the accompanying drawings and the description below. Other features and advantages will be apparent from the description and drawings, and from the claims.

DESCRIPTION OF DRAWINGS

Like reference numbers and designations in the various drawings indicate like elements.

DETAILED DESCRIPTION

Figure 1A:
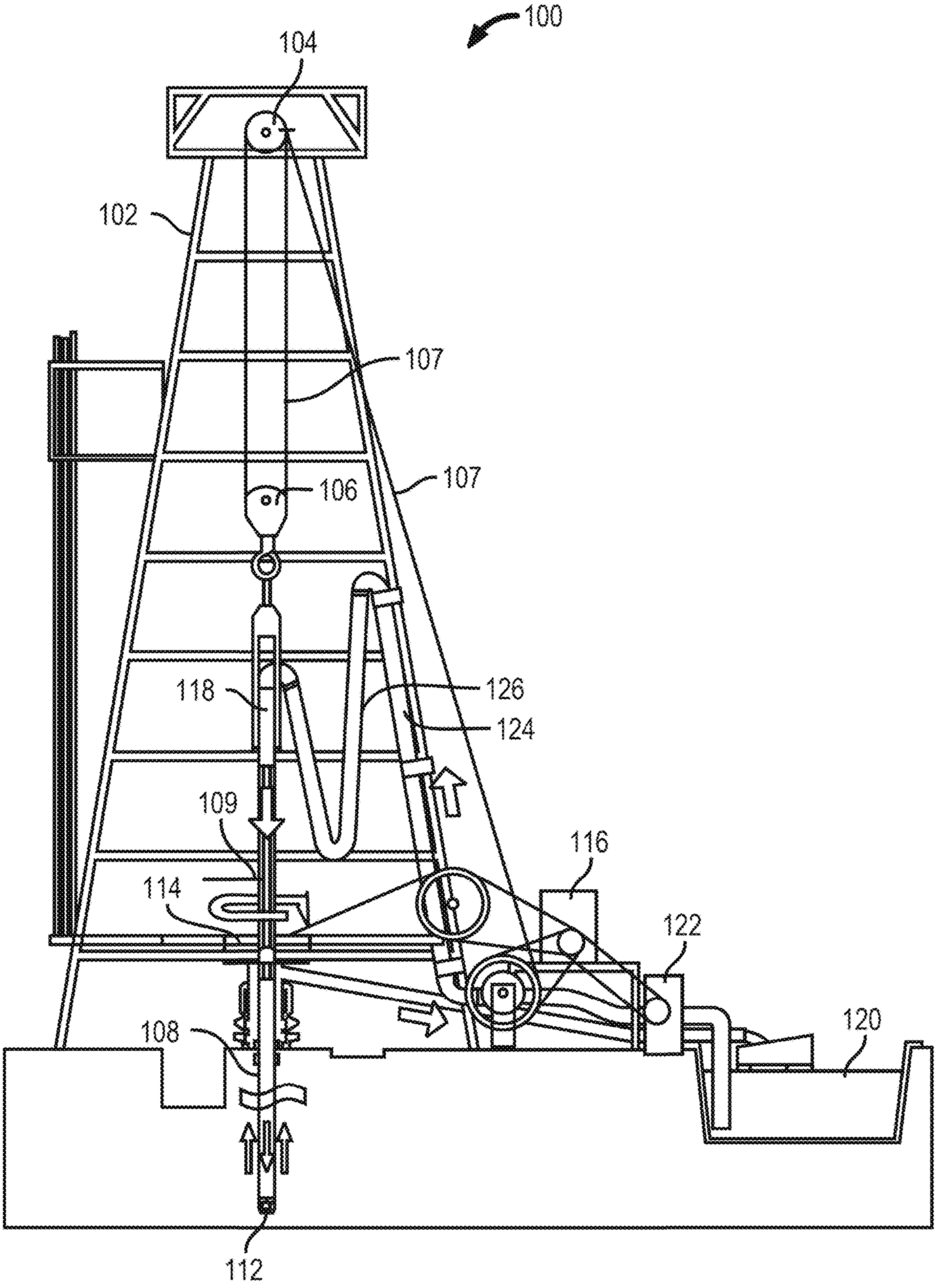
FIG. 1A is an illustration of an example well drilling rig.

Systems and methods described in this disclosure are configured for predicting reservoir quality related diagenesis based on extraction of data from thin-section (TS) images of the reservoir. A data processing system is configured to estimate a reservoir quality based on measuring parameter values for quartz overgrowth (QO), clay coating (CC), and visual porosity (VP) parameters from thin-section images of the open-hole (OH) log data. Specifically, the data processing system generates or builds a diagenesis model using imaging data obtained from the open-hole logs by extracting features of thin-section images that are correlated to the values of QO, CC, and VP parameters and correlating labeled open-hole log data to a model definition to train and validate the diagenesis model. Once the diagenesis model is validated with labeled OH log training data, the data processing system can apply the trained diagenesis model to unseen OH log data to predict values of QO, CC, and VP for a reservoir represented by the unseen OH log data. The values of QO, CC, and VP can represent a level of diagenesis in the reservoir which can be used to estimate a quality of the reservoir.

Diagenesis is the set of processes by which sediments evolve after they are deposited and begin to be buried. Diagenesis includes physical effects such as compaction and the deformation of grains in the sediment (or sedimentary rock), as well as chemical reactions such as the dissolution of grains and the precipitation of minerals to form cements in the sediment's pore space. The assessment of rock paragenesis (diagenetic history) is based, where possible, on cement stratigraphy, cross-cutting relationships of cements and replacement textures, recrystallization textures, and any structural fabrics that might be present.

Quartz overgrowth (QO) includes diagenetic processes that can be defined as the development of quartz cement around detrital grains, with the quartz cement growing in optical continuity with the grains that it has enclosed (authigenic overgrowth). This diagenesis has a strong impact on the permeability and porosity of the formation; in extreme cases, the primary porosity can be completely obliterated. Clean sandstone and quartzites are the most susceptible to this type of cementation.

Clay coating (CC) includes a diagenetic processes that happens during a very early phase of the burial process (e.g., eodiagenesis), mineralogical transformation happens to transform feldspars and original clay minerals into secondary products, mostly chlorite, illite, and smectite. Pore-filling clays can destroy a reservoir's quality by occluding intergranular space. CC happens when the phyllosilicate neoformation happens on the pore walls, somehow preserving the reservoir quality and preventing QO cementation.

The data processing system is configured to estimate a reservoir quality by predicting the values of the QO and CC parameters for the reservoir. Based on the estimated quality of the reservoir at given locations, one or more additional wells can be drilled, or production controlled.

FIG. 1A shows an illustration of an example well drilling rig 100. A derrick 102 provides a structure that supports the drilling equipment. A crown block 104 mounted at the top of the derrick 102, a traveling block 106, and a drill line 107 connected between them move the drill string 108 vertically. The drill string 108 includes a plurality of sections of drill pipe 110, a kelly bar 109, and a drill bit 112 or other bottom hole assembly. The kelly bar 109 is a square section of pipe that interfaces with a rotary table 114 to transfer torque from a motor or engine 116 to the drill string 108. A swivel 118 is connected between the top of the drill string 108 and the traveling block 106. The swivel 118 allows the drill string 108 to turn without turning the traveling block 106.

A drilling fluid or mud is used to remove cuttings from the well during drilling. A mud tank 120 holds the mud. A mud pump 122 pumps the mud from the mud tank 120 to the swivel 118 via a rigid standpipe 124 and a flexible hose 126. The mud is pumped through the center of the drill string 108 to the bottom of the hole through the drill bit 112. The mud returns to the surface carrying the cuttings through the annulus formed between the wall of the well and the outside of the drill string 108. The mud returns to the mud tank 120 via a flow line 128 where the cuttings are filtered, and the mud recirculates through the system.

As the drill string 108 rotates, the drill bit 112 engages with and cuts the bottom of the hole penetrating a subsurface formation. The rate at which the drill bit penetrates the formation is called the rate of penetration (ROP). The weight on the drill bit (WOB) is controlled by the amount of tension applied to the drill line 107 and can affect the ROP.

The motor or engine 116 that turns the drill bit and raises and lowers the drill string, the mud pump 122 and other equipment located on or near the drilling rig such as generators, burn fuel and emit carbon dioxide, CO2. The amount of CO2 emitted can be proportional to the fuel consumed by the drilling rig. Fuel consumption and CO2 emissions can be reduced by optimizing various drilling parameters.

Figure 1B:
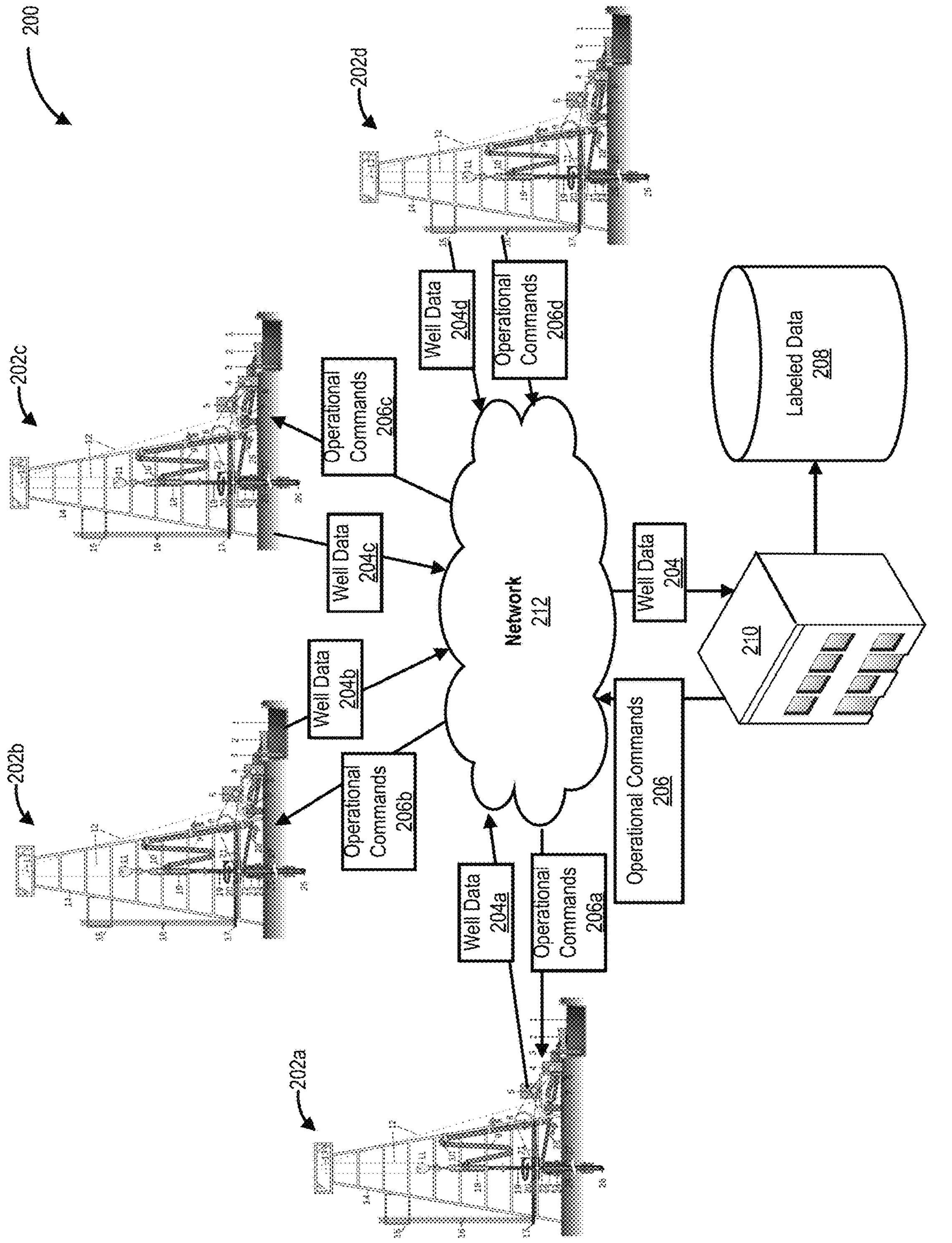
FIG. 1B is an illustration of an example system for hydrocarbon well production.

FIG. 1B shows a system 200 for hydrocarbon well production. The system 200 includes a plurality of wells 202*a-d* (collectively wells 202), a control center 210, and a network 212. The plurality of wells 202 are at various locations in a reservoir and can each include the well drilling rig 100 described in relation to FIG. 1A. Generally, each of the wells 202 includes one or more sensors that are configured to measure data during the drilling and production processes. The sensors of each well 202*a-d* are configured to measure respective well data 204*a-d* (collectively well data 204) such as flow rate in a wellbore, a wellbore pressure, a wellbore temperature, fluid composition, a well depth, and so forth. Each of the wells 202 sends respective well data 204*a-d* over the network 212 to the control center 210. The control center 210 includes a data processing system that is configured to receive the well data 204, process the well data, and generate operational commands 206*a-d* (collectively operational commands 206) for each of the respective wells 202*a-d*. The operational commands 206 are configured to control well production at each of the respective wells 204*a-d*. The well production is controlled based on an optimal well production that is determined by the data processing system at the control center 210. The optimal well production represents a maximum or nearly maximum well production that a given well can output based on the constraints of the reservoir and of the hardware at the actual well rig.

Responsive to the measured values of the respective production variables at a well, the data processing system of the control center 210 is configured to determine a target production for that well and one or more other wells at the reservoir. For example, the data processing system is configured to maximize oil production overall in a reservoir by monitoring production from each of the individual wells 202*a-d* within the reservoir. The data processing system is configured to periodically (or continuously) receive well data 204 from the wells 202, the process the well data using the optimization model subsequently described and update well production targets to optimize hydrocarbon output at the reservoir. The data processing system is configured to generate operational commands 206 that cause the wells 202 to produce at or near the respective target production rates specified by the output of the optimization model. The operational commands specify instructions that because the hardware at the respective wells 202*a-d* to pump water, extract hydrocarbons, or otherwise operate the well to achieve the specified target production.

The data processing system of the control center 210 controls operation of each of the wells 202 at a reservoir to maximize overall hydrocarbon production for the reservoir. For example, the data processing system can set production rates for a particular well 202*a-d* based on production rates set for one or more of the other wells 202*a-d* at the reservoir. In an example, the data processing system maximizes a hydrocarbon production for a particular well in the reservoir without accounting for production rates at one or more other wells at the reservoir.

The locations of the wells 202*a-d* can be selected in the reservoir based on the diagenesis model that specifies estimates of values for reservoir parameters at various locations in the reservoir, such as porosity values. Specifically, the data processing system executes a diagenesis model to predict the effects or level of diagenesis throughout the reservoir, predict the values of QO and CC (and in some examples, VP), and predict locations for further hydrocarbon exploration, such as a location for drilling a well 202.

Figure 2:
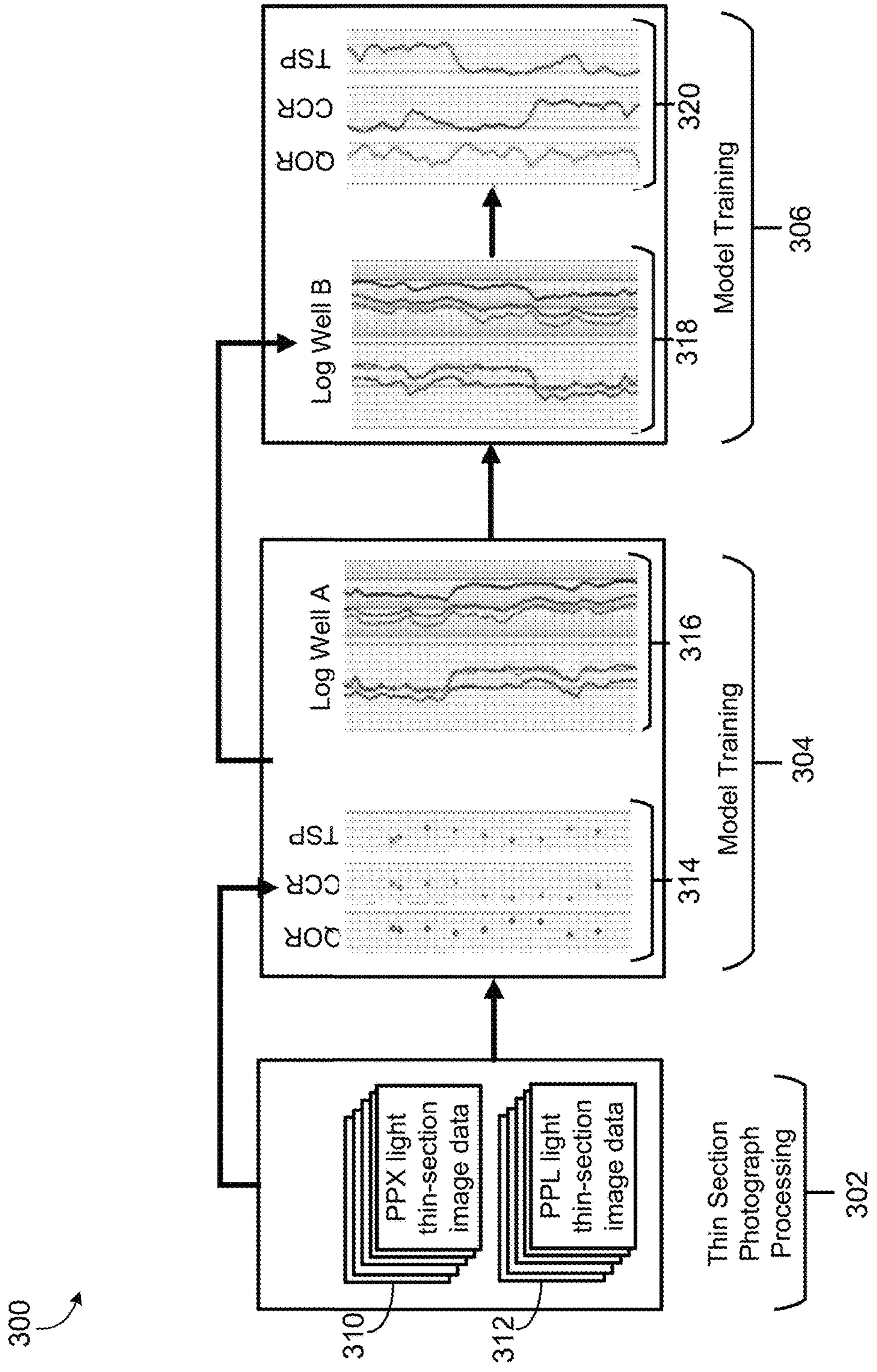
FIG. 2 is an illustration of an example process for diagenesis model generation and execution.

FIG. 2 is an illustration of an example process 300 for diagenesis model generation and execution to process open-hole well log data to estimate reservoir quality from predicted values for QO and CC parameters. The process 300 can be performed by one or more data processing systems as described herein.

The data processing system receives image data 302 including thin-section photographs from open-hole log data. The image data 302 include two types of images. The data processing system can process plain polarized light (PPL) images 310 and crossed polarized light (XPL or CPL) images 312 obtained from a (polarized) mineralogical microscope. A PPL image includes an image that is captured with a polarizer under the specimen and a polarizer (analyzer) above the specimen that are in-line with each other (0°). A CPL (or XPL) image includes an image that is captured with a polarizer under the specimen and a polarizer (analyzer) above the specimen that are crossed with each other (90°).

These two types of image data are used because there are benefits for determining parameter values for CO and CC. Different types of features are observable in each image type. Specifically, both images can be used simultaneously for the segmentation to improve object accuracy and definition with generation of an improved segmentation. The data processing system segments only borders that are common in both PPL and XPL images. This avoids over-segmentation. Briefly turning to FIG. 3C, in the PPL image 362, pore filling dye is visible (e.g., see regions 363*a-b* of image 362). The dyed regions 363*a-b* are identifiable by the data processing system. The data processing system can extract the pore objects by filtering on a color window corresponding to a dye color (e.g., blue) around the pores (e.g., by a filtering step 368). In a filtered image 364, the CC regions 363*a-b* appear as a regions 365*a-b* that are detected with a perimeter analysis around the pores by the data processing system. The XPL image 372 is used to identify quartz crystals from other minerals. Quartz crystals change colors in XPL depending on the plate rotation like many other mineral, but the color variation (Pleochroism) is always white-grey-black (extinction). The data processing system can identify crystals that show null or very low saturation as quartz without requiring analysis of multiple plate angles. The preprocessing steps of FIG. 3C are subsequently described in additional detail.

Returning to FIG. 2, the data processing system described herein (such as subsequently with respect to FIG. 5) is configured to execute a set of image processing techniques on the OH thin-section image data 302 to extract values for QO, CC, and VP properties in the reservoir. In some implementations, the data processing system uses a specific workflow of image processing and analysis steps to extract values for a ratio of QO particles to total particles in the thin-section image data, a ratio of coated perimeter to total perimeter values for the thin-section image data, and a ratio of the VP area to a total area in the thin-section image data. The data processing system uses these ratios to predict reservoir quality in regions without drilled wells or available open-hole log data. The image processing workflow is subsequently described in further detail in relation to FIGS. 3A-3B.

The data processing system is configured to generate a diagenesis model 304 for a reservoir. The diagenesis model 304 is configured to predict, from OH log data, a diagenesis occurring in a reservoir. The data processing system can estimate reservoir quality from the predicted diagenesis. The data processing system can use machine learning to build the diagenesis model. For example, a specific workflow of image processing and analysis can be used based on training data including thin-section image data. In some implementations, the process 300 is a precursor for a machine learning model and can generate labeled data for training those machine learning models. In another example, machine learning is not required. The data processing system builds the diagenesis model based on labeled thin-section image data.

The data processing system analyzes features of the thin-section image data using standalone image processing processes. FIG. 3C shows a process 360 for processing PPL images, such as image 362 for CC analysis. The pore filling dye is visible (e.g., in regions 363*a-b*). The data processing system can extract the pore objects (e.g., objects 365*a-b*) by filtering on a color window corresponding to the dye color. The data processing system detects the CC around the pores by a perimeter analysis around the pores, and the CC appears as dark or black objects, such as representative objects 365*a-b*. The data processing system determines the CC rate as a ratio between the coated pore perimeter and total pore perimeter of a thin section in image 364.

The process 370 for processing XPL images, such as image 372, for QO analysis in which the data processing system identifies quartz crystals from other minerals. Quartz crystals change colors in XPL images depending on a plate rotation, like some other minerals. The color variation (Pleochroism) is always white-grey-black (extinction). The crystals that show null or very low saturation, such as representative crystals 372*a-d* in image 372, are identifiable as quartz without analysis of multiple plate angles. The data processing system can analyze the perimeters of the identified crystals 372*a-d*. If the data processing system determines that the crystals 372*a-d* have a convex shape and an elongation ratio that exceeds a threshold ratio (e.g., 374*a* and 374*d*), the data processing system can determine that those qualifying crystals are quartz overgrowth. The data processing system determines that the other quartz particles (e.g., such as remaining quartz particles 374*b* and 374*c*) are quartz grains. The data processing system determines the QO rate determined to reference space not occupied by the quartz grains. This value can be determined as a ratio value of the total overgrowth particles to the value of the total thin section area minus the total quartz grains area:

$$QO \text{ rate} = \frac{\text{Total Overgrowth Particles Area}}{(\text{Total Thin Section Area} - \text{Total Quartz Grains Area})} \quad (1)$$

Returning to FIG. 2, the data processing system is configured to extract pore perimeters, quartz overgrowth perimeters, etc. to determine the level of diagenesis in a particular area. The data processing system uses automatic processes to extract quantitative data from TS image data, rather than requiring diagenetic facies through petrological analysis of thin sections.

The data processing system is configured to generate quantitative information for diagenesis level classification from the TS image data 302 without requiring open-hole logs petrophysical analysis. The quantification of QO rate and CC rate 314 from TS image data 302 are used to label OH log data 316 to build or train the diagenesis model 304. The data processing system chooses OH log data after geological and petrophysical assumptions have been processed for standard borehole corrections.

Different levels of diagenesis can be classified, and the prediction output data look like represent probabilities values. There are fields of existence related to the natural phenomena. For example, CC occurs early in diagenesis and can prevent quartz overgrowth. When a rock has 100% quartz overgrowth, there are no pores, and the CC value is 0.

In some implementations, the data processing system uses morphological measurements which are extracted from the TS image data 302. Being the overgrowth silica growing around the grains, the OC have a convex-hull index and an elongation different from the silica grains. The data processing system performs segmentation of the image and objects of interest (OOI) are identified that show achromatic red-green-blue (RGB) values for the crossed polarity image (PPX). This is contrasted with a plane polarized light (PPL) mode of a polarizing microscope. The achromatic RGB sequence of the PPX image is the quartz extinction sequence: black-gray-white. In a given formation, other minerals always have polarization colors and are not achromatic. The data processing system can use this approach to avoid use of artificial intelligence and machine learning that can require a large amount of training data and that can require human labeling of training data, which can reduce a quality and quantity of the training data.

In some implementations, clay coating can be observed and reported in both thin-sections and scanning electron microscope (SEM) images. SEM images can provide limited value for valid upscaling. To overcome this limitation, the data processing system executes a workflow that uses pore-perimeter analysis based on image-processing without requiring machine learning. The CC rate is determined based on pore analysis rather than grain analysis and considers measurements of all the pores included in the thin section images.

The data processing system is configured to apply the diagenesis model 306 to predict the diagenesis level in a reservoir based on receiving new input log data 318. The data processing system is configured to generate output predictions data 320 for each of the QOR, CCR, and thin-section porosity (TSP) values throughout a reservoir based on the data from the unseen OH logs 318 that include borehole data (e.g., from wells 202 of FIG. 1B).

The data processing system uses the values of the diagenesis parameters QOR, CCR, and TSP to generate an estimate of a reservoir quality at various locations in the reservoir. Reservoir quality is related to the determined values of QOR, CCR, and TSP. Specifically, reservoir quality represents an ability of a reservoir to store fluid and/or allow fluid flow. Porosity and permeability are amongst the main parameters reprinting reservoir quality, with higher porosity and higher permeability usually correlating to higher reservoir quality. Clay coating and quartz overgrowth, or a combination thereof, have a direct impact on both permeability and porosity. Quartz overgrowth can obliterate porosity, reduce pore connection, and increase the flow tortuosity, reducing the subsurface permeability. Clay coating reduces the pore volume and reduce or obstruct the pore having a direct impact on porosity and permeability as well.

Figure 3A:
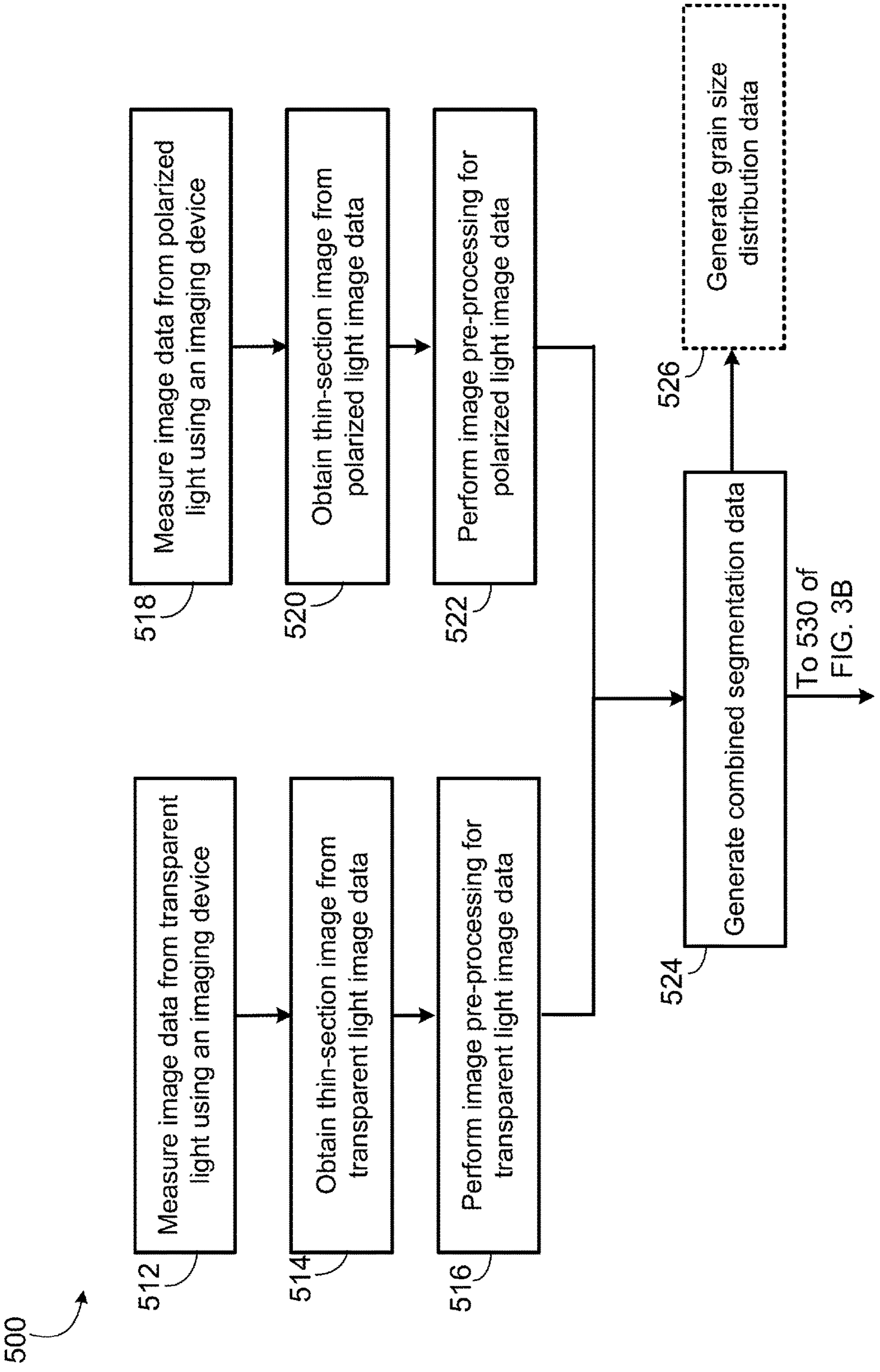
FIG. 3A is an illustration of an example process for diagenesis model generation from image data.
Figure 3B:
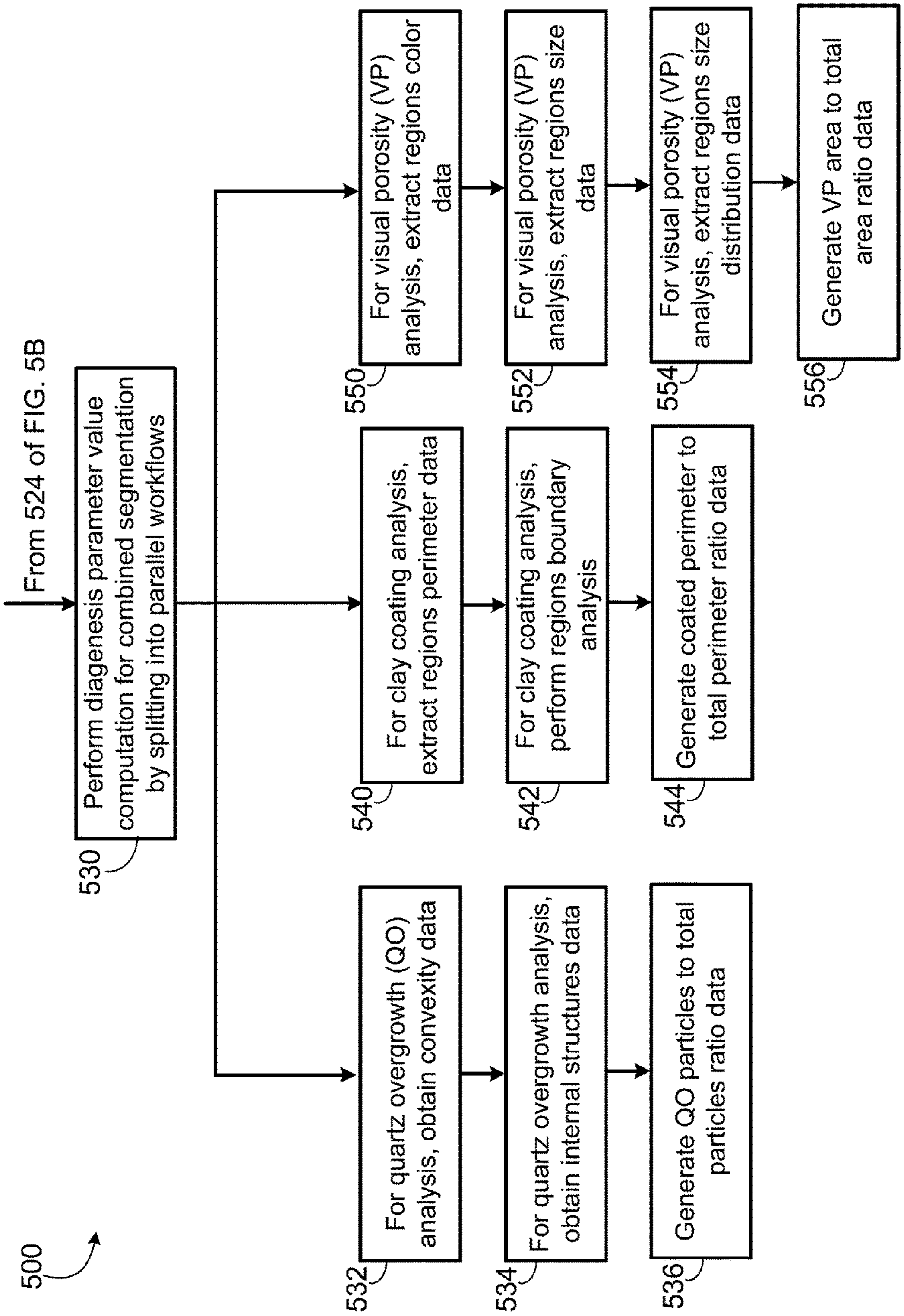
FIG. 3B is an illustration of an example process for diagenesis model generation from image data.
Figure 3C:
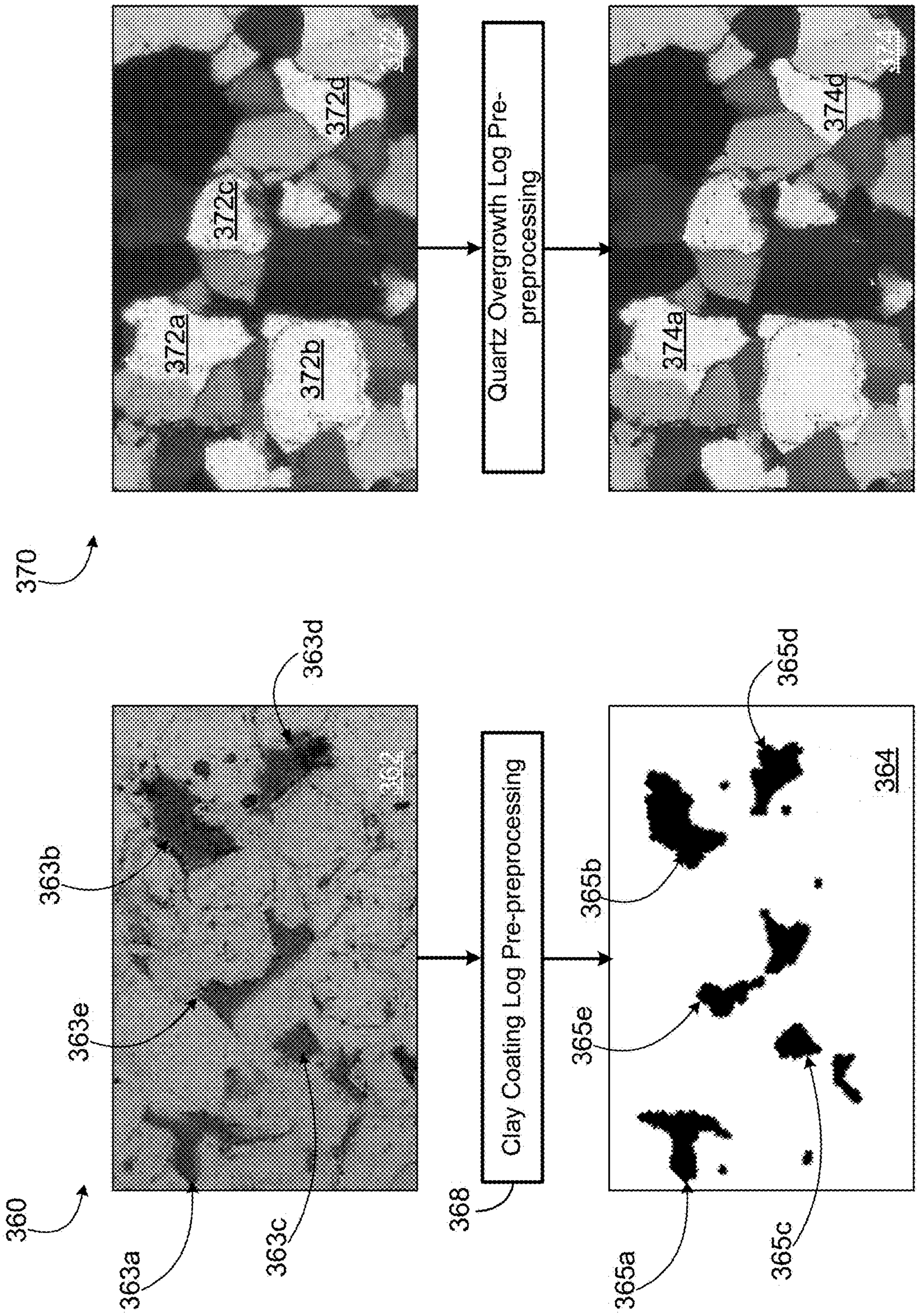
FIG. 3C shows example images illustrating preprocessing for quartz overgrowth logs and clay coating logs.

FIGS. 3A-B illustrate an example process 500 for diagenesis model generation from image data. In some implementations, the process 500 can be performed by a data processing system, such as data processing system 600 of FIG. 5. The data processing system performs a set of image processing processes for extracting values of diagenesis parameters including each of QOR, CCR, and TSP.

The data processing system performs thin-section automated parameter extraction as now described. An image processing-based algorithm approach is described. However, results from this method can also be used to implement a machine learning-based model for the QOR value determination and the CCR value determination. During the processing, the visual porosity (VP) is extracted from the image by filtering blue zones of the images.

In process 500, the data processing system determines the QOR, CCR, and TSP. QOR is based on shape convexity analysis and object topology. A main index used is solidity. Solidity includes a ratio of pixels in the objects to pixels in a convex hull image. Solidity represents a measure of a compactness of an object. Quartz overgrowths are not solid objects and are distinguished by grains by where the QOs grow. QO layers share at least one side with the contiguous grain. To perform these measurements, the data processing system segments the image into each particle and pore, and the following process is applied to each segment. The data processing system uses a cut-off value to split the QO layers from the grains. A QO Rate (QOR) is defined as the ratio between the total area of the QO particles and the total picture area minus the grain area. When QOR is equal to 1 (100%), all space that is not classified as grain is occluded, and therefore there is no porosity.

The CCR processing workflow is based on pores identification and perimeter analysis from the PPL thin section image. The TSP is computed based on the following. The data processing system identifies the pores by thresholding a typical blue color and segmenting the image for each pore space. After the perimeter around the pore is analyzed, the dark pixels of the clay layers are recognized as clay coating and accounted for in the CCR computation. This phase has two outputs: TSP, as the ratio between the total identified pores are and the total area of the picture, and CCR, as the ratio between the pores perimeters with black pixels (clay minerals) and total pores perimeter. Each of the workflows for determining QOR, CCR, and TSP is subsequently described.

The data processing system 500 performs the following steps for QOR, CCR, and TSP parameter value determination from thin section images. The data processing system measures (512) image data from PPL light image data using a camera, as previously described in relation to FIG. 3C.

The data processing system obtains (514) thin-section image from PPL and PPX light image data. The data processing system performs (516) image pre-processing for PPL light image data. The image pre-processing steps include the following. To prepare the images subsequent segmentation, the data processing system, in process 360, color thresholds the image 362 on the dye color of the dye in the pores (e.g., representative pores 363*a-e*). The data processing system generates a binary pore mask to extract pores data (e.g., representative pores data 365*a-d*).

The data processing system measures (518) image data from PPX light image data using a camera. The data processing system obtains (520) thin-section image from PPX light image data. The data processing system performs (522) image pre-processing for PPL light image data. The image pre-processing steps include the following. As shown in process 370 of FIG. 3C, the data processing system pre-processes the PPX images by the following steps for subsequent segmentation. The data processing system removes noise from image 372 while preserving borders with a bilateral filter and performs a color reduction (posterization) to generate image 374.

The data processing system then performs advanced segmentation 524 using one or both thin section images (PPX light image data or PPL light image data). In some implementations, the data processing system generates (526) grain size distribution data.

The data processing system performs (530) diagenesis parameter value computation for combined segmentation by splitting into parallel workflows including a first workflow for QOR value determination, a second workflow for CCR value determination, and optionally a third workflow (combinable with the second workflow) for TSP value determination.

The QOR workflow is now described. The data processing system, for quartz overgrowth (QO) analysis, obtains (532) convexity data from the segmented TS image. The data processing system, for quartz overgrowth analysis, obtains (534) internal structures data of the QO from the TS image data. From these data, the data processing system performs a solidity computation. Solidity is defined as image area divided by convex hull area. Solidity can vary between 0 and 1, wherein 1 occurs without any convexity.

The data processing system performs a proximity computation. In some implementations, the data processing system performs a nearest neighbor graph (NNG). However, other approaches can be used for refinement. Other examples performed after segmentation can generate similar results with varying performance, These examples can include Kirkpatrick's algorithm, Voronoy diagrams, Delaunay triangulations, Euclidean minimum spanning tree (EMST), relative neighborhood graph (RNG), a Gabriel graph (GG) slab-based methods, trapezoidal maps, separating chains, and so forth.

The data processing system performs a QO particles identification as described previously. Specifically, the data processing system performs segmentation for the images (shown in FIG. 3C, determines a solidity of subsurface, and applies a solidity cutoff threshold. In some implementations, the threshold can be 0.5. In some implementations, the threshold can be any value between 0.3 to 0.8. In some implementations, the parameter is binary with two very well separated clusters, and the exact threshold may be adjusted as needed.

The data processing system generates (536) QO particles to total particles ratio data that represents the QOR. The QOR value is then compared to OH log data for the reservoir to build the diagenesis model.

The data processing system determines a thin section porosity (TSP) and clay coating rate (CCR) based on the following steps of process 500. The data processing system is configured, for clay coating analysis, to extract (540) regions perimeter data. The perimeter data can include a set (e.g., a list) of pixels (e.g., x, y coordinates) at a border of each pore, included a value determined as a nearest peak of the two-dimensional derivative.

The data processing system is configured, for clay coating analysis, to perform (542) regions boundary analysis. The data processing system starts from the perimeter pixels. As an outer thickness is added, more pixels are added to the set. The updated (augmented) pixel set is the boundary (outer) region.

The data processing system is configured to generate (544) a coated perimeter to total perimeter ratio data. The CCR value is then compared to OH log data for the reservoir to build the diagenesis model. FIG. 3C shows example data images used for processing.

The data processing system determines a thin section porosity (TSP) and clay coating rate (CCR) based on the following steps of process 500. The data processing system, for visual porosity (VP) analysis, extracts (550) regions color data from the segmented images. The data processing system, for visual porosity (VP) analysis, extracts (552) regions size data from the images. The data processing system, for visual porosity (VP) analysis, extracts regions size distribution data from the segmented images. The data processing system generates VP area to total area ratio data, representing the TSP values.

Figure 4:
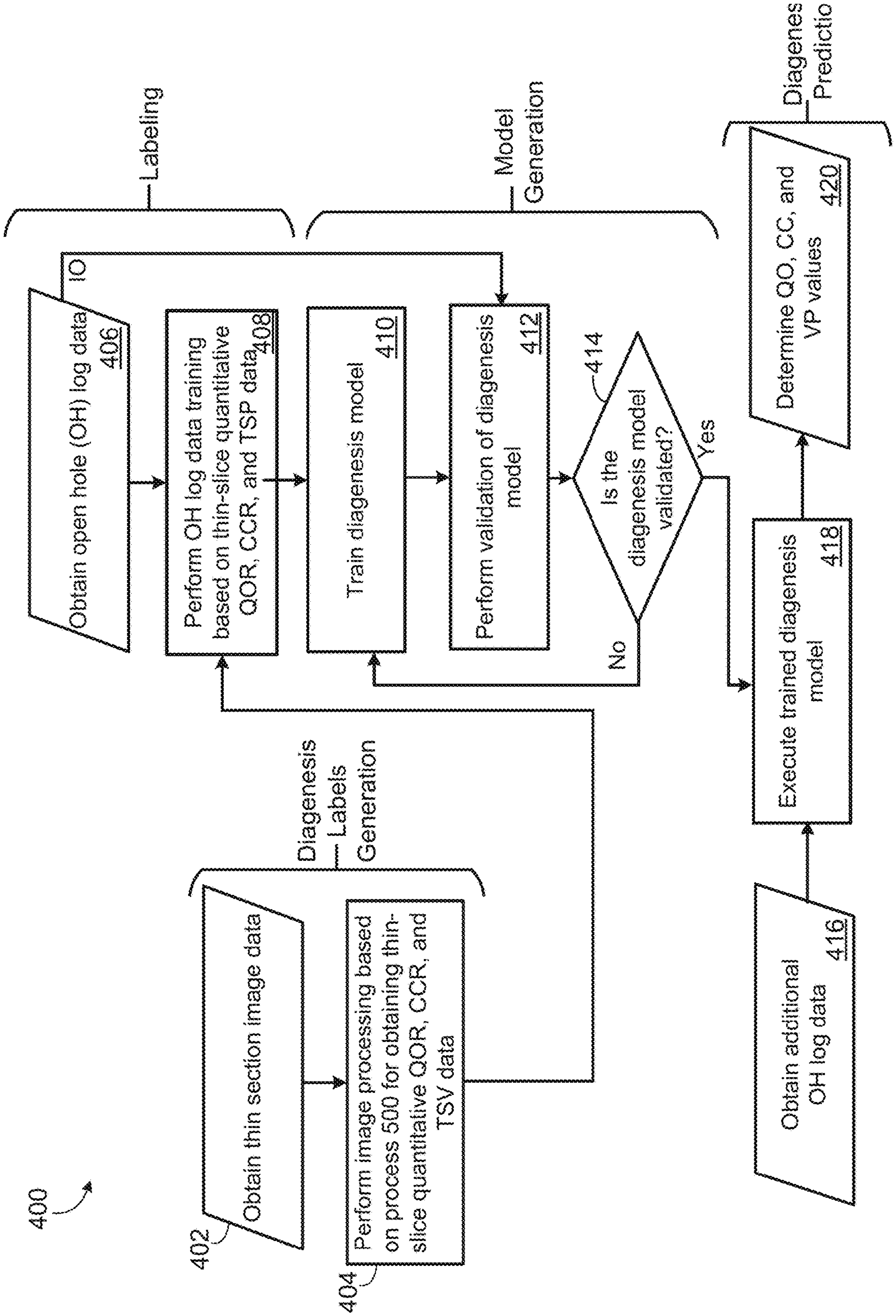
FIG. 4 is an illustration of an example process for diagenesis model generation and execution.

FIG. 4 shows flow diagram illustrating an example process 400 for training a data processing model for diagenesis level classification, such as by the data processing system 600 of FIG. 5, subsequently described. All data extracted from the thin section analysis is labeled with a proper depth, and the depth can now be used for the model implementation.

The process 400 is configured to train and validate a diagenesis model using labeled OH log data and then execute the trained model on new OH log data. The diagenesis model is trained as now described.

The data processing system obtains (402) TS image data. The data processing system performs (404) image processing based on the process 500 described in relation to FIGS. 3A-3B. The data processing system obtains, based on the image processing, TS quantitative QOR, CCR, and TSP values. These values, based on the QO, CC, and VP values, and input into the diagenesis model and correlated with obtained (406) OH log data.

Open logs data obtained and used in this application are correlated to matrix and clay typing. Measurements such as sonic, background resistivity from borehole images, and density are directly correlated to matrix compactness, while GR spectroscopy, Thorium concentration, and Potassium concentration are sensitive to clay typing change. Any logs with similar sensitivity to matrix and clay type can be used for labeling. A representative (but non exhaustive), list of relevant logs can include the following for training the model for each diagenesis parameter. For clay coating, the logs can include a thorium concentration log, a potassium concentration log, a shear slowness log, and a photoelectric absorption properties (PEF) log. For quartz overgrowth, the logs can include a thorium concentration log, a potassium concentration log, a sonic shear slowness log, a sonic compressional slowness log, and/or a density log. For visual porosity, the logs can include a sonic shear slowness log, a sonic compressional slowness log, a nuclear magnetic resonance (NMR) log, a dielectric log, and a density log.

The diagenesis model is trained (410) using the correlated/labeled log data and extracted QOR, CCR, and TSP values data. The data processing system determines thin section QO, CC, and TSP values (called the target data). The data processing system selects open-hole logs. The data processing system extracts logs values at a same thin section depth to generate input data. The data processing system selects a model for processing the data as previously described. The data processing system performs a data transformation (e.g., normalization) if needed. The data processing system trains the selected model (e.g., a machine learning model). The data processing system optimizes the trained model as needed by using additional log data if validation indicates further training is to be performed.

After the logs are labeled and the model is trained with the QOR, CCR, and TSP values, a blind test (or other method) is performed on a known dataset to validate (412) the performance and accuracy. The model is validated to be within a threshold (414) accuracy level. Accuracy in this example represents how often the machine learning model correctly predicts the outcome. The desired range is at least between 70% and 90%.

Once the model is validated, the model can be used to predict the diagenesis parameters and synthesize the respective logs. The data processing system obtains (416) unlabeled, new OH log data. The data processing system executes (418) the trained diagenesis model on the new log data. The data processing system determines (420) values for the QO, CC, and VP parameters. As described previously, the reservoir quality can be obtained from the diagenesis classification represented by the values of the QO, CC, and VP parameters.

Figure 5:
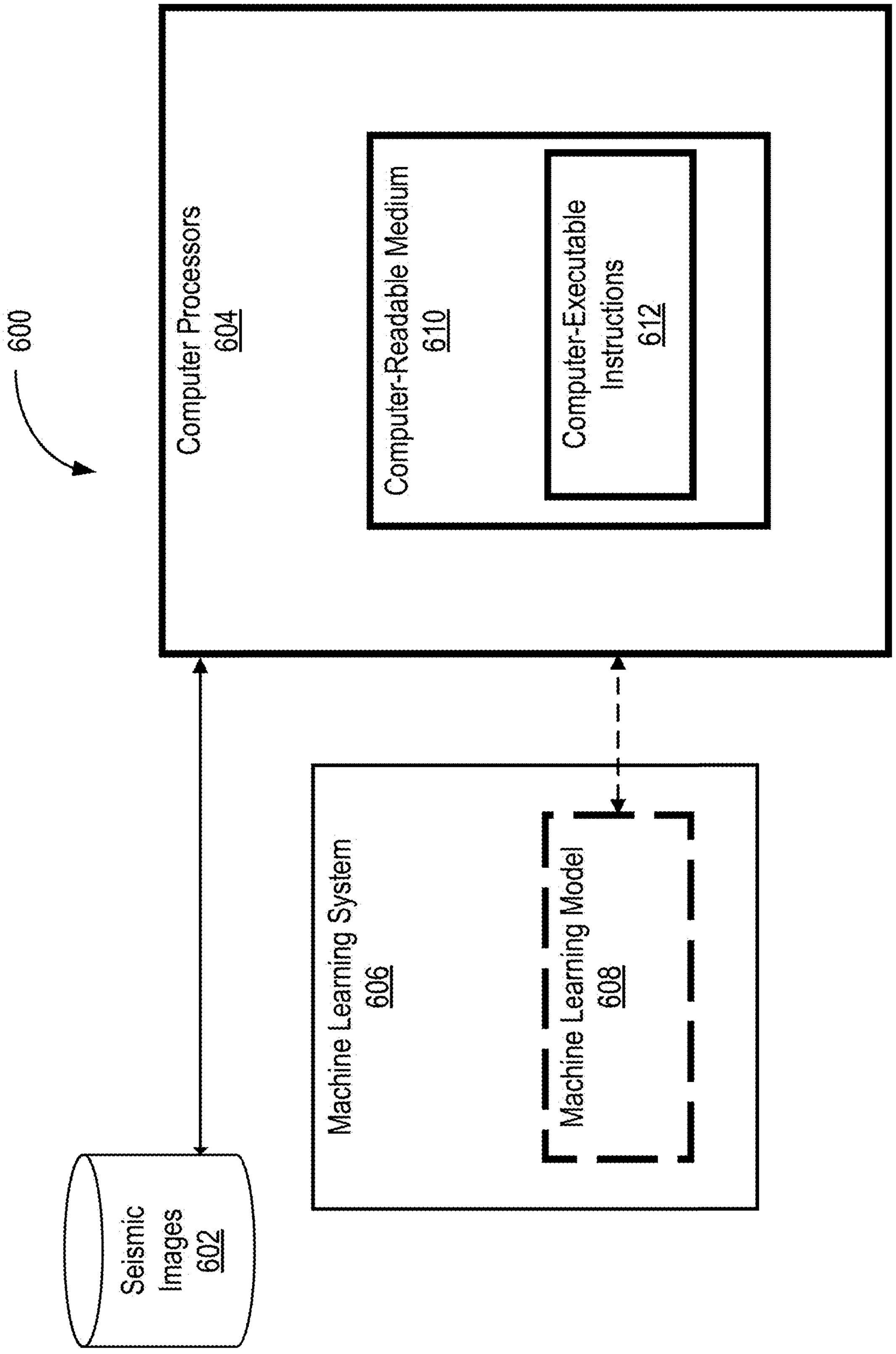
FIG. 5 is a block diagram illustrating a data processing system.

FIG. 5 shows an illustration of a data processing system 600. The data processing system 600 can be configured to execute the processes 400, 500 described previously for a diagenesis level classification of a reservoir.

The data processing system 600 is configured to execute a machine learning model 608, such as the data processing models described previously in relation to FIG. 5. Generally, the data processing system 600 is configured to process seismic image data 602 and determine a set of predictions for what a diagenesis parameter value is for a given image. The system 600 includes computer processors 604. The computer processors 604 include computer-readable memory 610 and computer readable instructions 612. The system 600 also includes a machine learning system 606. The machine learning system 606 includes a machine learning model 608. The machine learning model 608 can be separate from or integrated with the computer processors 604.

The computer-readable medium 610 (or computer-readable memory) can include any data storage technology type which is suitable to the local technical environment, including but not limited to semiconductor based memory devices, magnetic memory devices and systems, optical memory devices and systems, fixed memory, removable memory, disc memory, flash memory, dynamic random-access memory (DRAM), static random-access memory (SRAM), electronically erasable programmable read-only memory (EEPROM) and the like. In an embodiment, the computer-readable medium 610 includes code-segment having executable instructions.

The machine learning system 606 is capable of applying machine learning techniques to train the machine learning model 608, as described in relation to FIG. 4. As part of the training of the machine learning model 608, the machine learning system 606 forms a training set of input data by identifying a positive training set of input data items that have been labeled to have the property in question, QOR values, CCR values, or TSP values, and, in some embodiments, forms a negative training set of input data items that lack the property in question.

The machine learning system 606 extracts feature values from the input data of the training set, the features being variables deemed potentially relevant to whether or not the input data items have the associated property or properties. An ordered list of the features for the input data is herein referred to as the feature vector for the input data. In one embodiment, the machine learning system 606 applies dimensionality reduction (e.g., via linear discriminant analysis (LDA), principal component analysis (PCA), or the like) to reduce the amount of data in the feature vectors for the input data to a smaller, more representative set of data.

Figure 6:
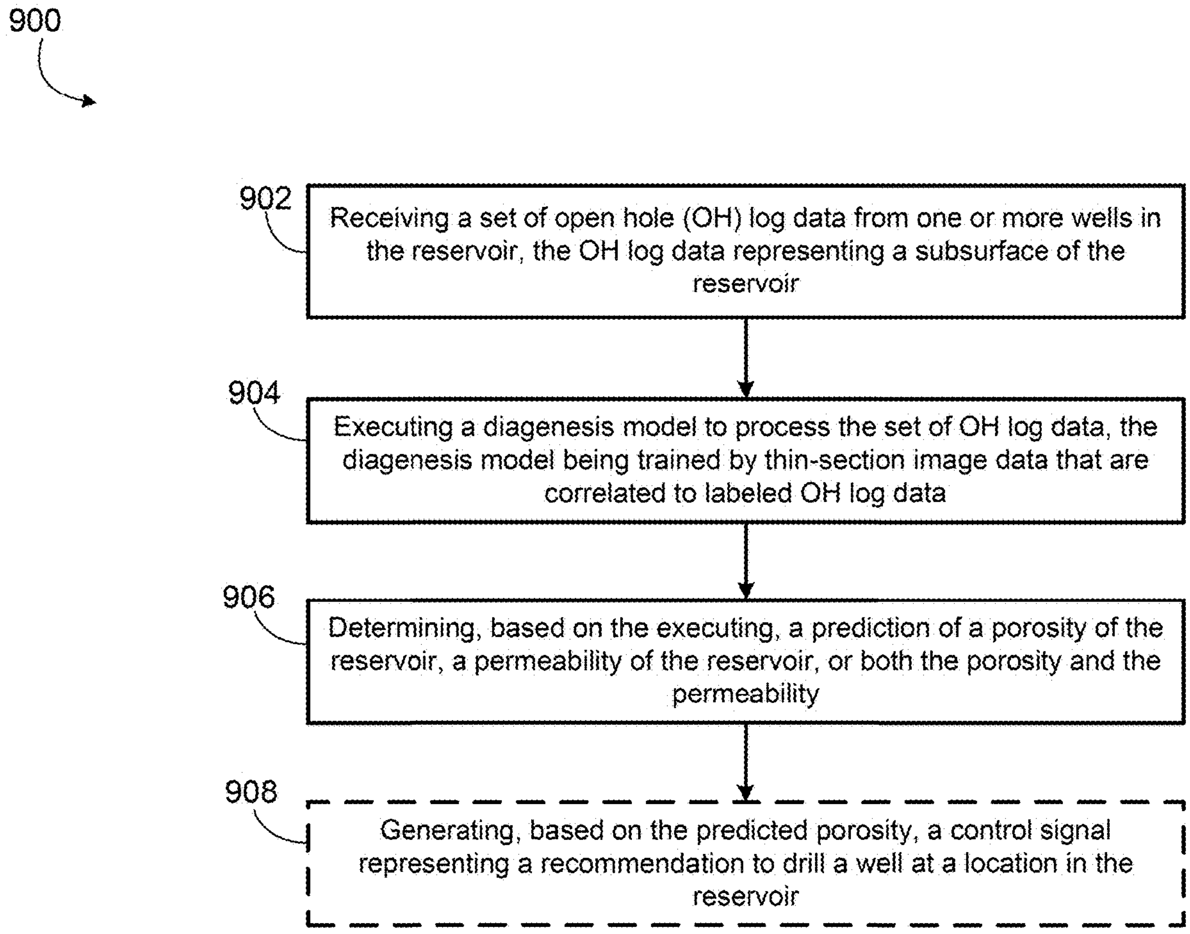
FIG. 6 is an illustration of an example process for diagenesis model generation.

FIG. 6 is an illustration of an example process 900 for diagenesis model generation. In some implementations, the process 900 is performed by the data processing systems described herein, such as the data processing system 600 of FIG. 4. The process 900 is for determining a diagenesis level in a reservoir for performing hydrocarbon extraction. The process 900 includes receiving (902) a set of open hole (OH) log data from one or more wells in the reservoir. The OH log data can represent a subsurface of the reservoir. The process 900 includes executing a diagenesis model to process the set of OH log data. The diagenesis model can be trained by thin-section image data that are correlated to labeled OH log data, the labeling identifying values for a quartz overgrowth rate (QOR), a clay coating rate (CCR), or a thin-section porosity in the subsurface based on a value in the OH log data and a type of the OH log. The process 900 includes determining (906), based on the executing, a prediction of a porosity of the reservoir, a permeability of the reservoir, or both the porosity and the permeability. The process 900 includes generating (908), based on the predicted porosity, a control signal representing a recommendation to drill a well at a location in the reservoir.

In some implementations, the process 900 includes, based on the predicted diagenesis level in the reservoir, generating a control signal configured for causing drilling of a well in the reservoir corresponding to a location a higher values of QOR, CCR, or VP relative to another location in the reservoir.

In some implementations, the diagenesis model is trained by operations comprising: obtaining image data from an imaging device, the image data representing at least a portion of a subsurface of the reservoir; obtaining at least one thin-section image from the image data; segmenting the thin-section image into a set of segments, each segment of the set including at least one grain; extracting, from a segment of the set, first data representing a first ratio of quartz overgrowth particles to total particles; extracting, from the segment of the set, second data representing a second ratio of a clay coated perimeter value to a total perimeter value; and training the diagenesis model based on the first ratio and the second ratio to predict the diagenesis level in the subsurface of the reservoir.

In some implementations, the process 900 includes determining a visual porosity value for the portion of the subsurface of the reservoir by: extracting region color data from the segment of the set; filtering the segment of the set to remove blue color data from the segment; extracting a region size data from the segment of the set based on the filtering; determining a region size distribution based on the region size data; and determining a third ratio of the visual porosity area to a total area, wherein the third ratio represents a thin-section porosity value, and wherein a reservoir quality is based on the thin-section porosity value.

In some implementations, the OH log data comprises one or more of a thorium concentration log, a potassium concentration log, a shear slowness log, and a photoelectric absorption properties log.

In some implementations, the OH log data comprises one or more of a thorium concentration log, a potassium concentration log, a sonic shear slowness log, a sonic compressional slowness log, and/or a density log.

In some implementations, the OH log data comprises one or more of a sonic shear slowness log, a sonic compressional slowness log, a nuclear magnetic resonance (NMR) log, a dielectric log, and a density log In some implementations, the machine learning model 608 is based on a convolutional neural network (CNN) wherein the network parameter is a distribution, as described previously. A CNN can be configured based on a presumption that inputs to the CNN correspond to image pixel data for an image or other data that includes features at multiple spatial locations. For example, sets of inputs can form a multi-dimensional data structure, such as a tensor, which represent color features of an example digital image (e.g., a seismic image or set of seismic images). In some implementations, inputs to the CNN correspond to a variety of other types of data, such as logging while drilling (LWD) data, resistivity data, or various types of one-dimensional or multiple dimensional data. A convolutional layer of the CNN can process the inputs to transform features of the image that are represented by inputs of the data structure. For example, the inputs are processed by performing dot product operations using input data along a given dimension of the data structure and a set of parameters for the convolutional layer.

Performing computations for a convolutional layer can include applying one or more sets of kernels to portions of inputs in the data structure. The manner in which CNN performs the computations can be based on specific properties for each layer of an example multi-layer neural network or deep neural network that supports deep neural net workloads. A deep neural network can include one or more convolutional towers (or layers) along with other computational layers. In particular, for example computer vision applications, these convolutional towers often account for a large proportion of the inference calculations that are performed. Convolutional layers of a CNN can have sets of artificial neurons that are arranged in three dimensions, a width dimension, a height dimension, and a depth dimension. The depth dimension corresponds to a third dimension of an input or activation volume and can represent respective color channels of an image. For example, input images can form an input volume of data (e.g., activations), and the volume has dimensions 32×32×3 (width, height, depth respectively). A depth dimension of 3 can correspond to the RGB color channels of red (R), green (G), and blue (B).

In general, layers of a CNN are configured to transform the three dimensional input volume (inputs) to a multi-dimensional output volume of neuron activations (activations). For example, a 3D input structure of 32×32×3 holds the raw pixel values of an example image, in this case an image of width 32, height 32, and with three color channels, R, G, and B. A convolutional layer of a CNN of the machine learning model 608 computes the output of neurons that may be connected to local regions in the input volume. Each neuron in the convolutional layer can be connected only to a local region in the input volume spatially, but to the full depth (e.g., all color channels) of the input volume. For a set of neurons at the convolutional layer, the layer computes a dot product between the parameters (weights) for the neurons and a certain region in the input volume to which the neurons are connected. This computation may result in a volume such as 32×32×12, where 12 corresponds to a number of kernels that are used for the computation. A neuron's connection to inputs of a region can have a spatial extent along the depth axis that is equal to the depth of the input volume. The spatial extent corresponds to spatial dimensions (e.g., x and y dimensions) of a kernel.

A set of kernels can have spatial characteristics that include a width and a height and that extends through a depth of the input volume. Each set of kernels for the layer is applied to one or more sets of inputs provided to the layer. That is, for each kernel or set of kernels, the machine learning model 608 can overlay the kernel, which can be represented multi-dimensionally, over a first portion of layer inputs (e.g., that form an input volume or input tensor), which can be represented multi-dimensionally. For example, a set of kernels for a first layer of a CNN may have size 5×5×3×16, corresponding to a width of 5 pixels, a height of 5 pixel, a depth of 3 that corresponds to the color channels of the input volume to which to a kernel is being applied, and an output dimension of 16 that corresponds to a number of output channels. In this context, the set of kernels includes 16 kernels so that an output of the convolution has a depth dimension of 16.

The machine learning model 608 can then compute a dot product from the overlapped elements. For example, the machine learning model 608 can convolve (or slide) each kernel across the width and height of the input volume and compute dot products between the entries of the kernel and inputs for a position or region of the image. Each output value in a convolution output is the result of a dot product between a kernel and some set of inputs from an example input tensor. The dot product can result in a convolution output that corresponds to a single layer input, e.g., an activation element that has an upper-left position in the overlapped multi-dimensional space. As discussed above, a neuron of a convolutional layer can be connected to a region of the input volume that includes multiple inputs. The machine learning model 608 can convolve each kernel over each input of an input volume. The machine learning model 608 can perform this convolution operation by, for example, moving (or sliding) each kernel over each input in the region.

The machine learning model 608 can move each kernel over inputs of the region based on a stride value for a given convolutional layer. For example, when the stride is set to 1, then the machine learning model 608 can move the kernels over the region one pixel (or input) at a time. Likewise, when the stride is 2, then the machine learning model 608 can move the kernels over the region two pixels at a time. Thus, kernels may be shifted based on a stride value for a layer and the machine learning model 608 can repeatedly perform this process until inputs for the region have a corresponding dot product. Related to the stride value is a skip value. The skip value can identify one or more sets of inputs (2×2), in a region of the input volume, that are skipped when inputs are loaded for processing at a neural network layer. In some implementations, an input volume of pixels for an image can be "padded" with zeros, e.g., around a border region of an image. This zero-padding is used to control the spatial size of the output volumes.

As discussed previously, a convolutional layer of CNN is configured to transform a three dimensional input volume (inputs of the region) to a multi-dimensional output volume of neuron activations. For example, as the kernel is convolved over the width and height of the input volume, the machine learning model 608 can produce a multi-dimensional activation map that includes results of convolving the kernel at one or more spatial positions based on the stride value. In some cases, increasing the stride value produces smaller output volumes of activations spatially. In some implementations, an activation can be applied to outputs of the convolution before the outputs are sent to a subsequent layer of the CNN.

An example convolutional layer can have one or more control parameters for the layer that represent properties of the layer. For example, the control parameters can include a number of kernels, K, the spatial extent of the kernels, F, the stride (or skip), S, and the amount of zero padding, P. Numerical values for these parameters, the inputs to the layer, and the parameter values of the kernel for the layer shape the computations that occur at the layer and the size of the output volume for the layer. In some implementations, the spatial size of the output volume is computed as a function of the input volume size, W, using the formula (W−F+2P)/S+1. For example, an input tensor can represent a pixel input volume of size [227×227×3]. A convolutional layer of a CNN can have a spatial extent value of F=11, a stride value of S=4, and no zero-padding (P=0). Using the above formula and a layer kernel quantity of K=116, the machine learning model 608 performs computations for the layer that results in a convolutional layer output volume of size [55×55×156], where 55 is obtained from [(227−11+0)/4+1=55].

The computations (e.g., dot product computations) for a convolutional layer, or other layers, of a CNN involve performing mathematical operations, e.g., multiplication and addition, using a computation unit of a hardware circuit of the machine learning model 608. The design of a hardware circuit can cause a system to be limited in its ability to fully utilize computing cells of the circuit when performing computations for layers of a neural network.

Figure 7:
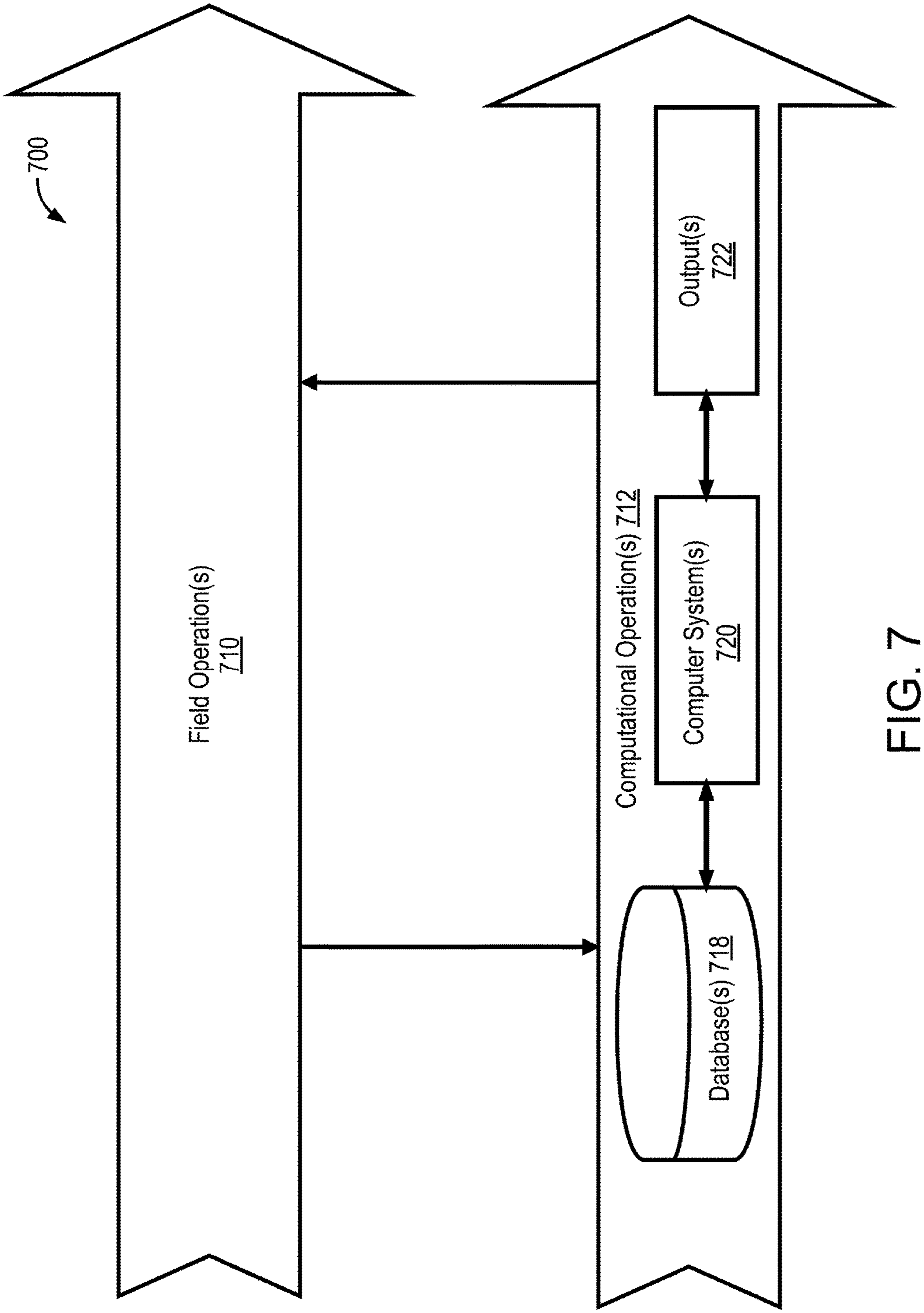
FIG. 7 illustrates hydrocarbon production operations.

FIG. 7 illustrates hydrocarbon production operations 700 that include both one or more field operations 710 and one or more computational operations 712, which exchange information and control exploration to produce hydrocarbons. In some implementations, outputs of techniques of the present disclosure (e.g., the method 300) can be performed before, during, or in combination with the hydrocarbon production operations 700, specifically, for example, either as field operations 710 or computational operations 712, or both. For example, the processes 300, 400 collect data during field operations, processes the data in computational operations, and can determine locations to perform additional field operations.

Examples of field operations 710 include forming/drilling a wellbore, hydraulic fracturing, producing through the wellbore, injecting fluids (such as water) through the wellbore, to name a few. In some implementations, methods of the present disclosure can trigger or control the field operations 710. For example, the methods of the present disclosure can generate data from hardware/software including sensors and physical data gathering equipment (e.g., seismic sensors, well logging tools, flow meters, and temperature and pressure sensors). The methods of the present disclosure can include transmitting the data from the hardware/software to the field operations 710 and responsively triggering the field operations 710 including, for example, generating plans and signals that provide feedback to and control physical components of the field operations 710. Alternatively, or in addition, the field operations 710 can trigger the methods of the present disclosure. For example, implementing physical components (including, for example, hardware, such as sensors) deployed in the field operations 710 can generate plans and signals that can be provided as input or feedback (or both) to the methods of the present disclosure.

Examples of computational operations 712 include one or more computer systems 720 that include one or more processors and computer-readable media (e.g., non-transitory computer-readable media) operatively coupled to the one or more processors to execute computer operations to perform the methods of the present disclosure. The computational operations 712 can be implemented using one or more databases 718, which store data received from the field operations 710 and/or generated internally within the computational operations 712 (e.g., by implementing the methods of the present disclosure) or both. For example, the one or more computer systems 720 process inputs from the field operations 710 to assess conditions in the physical world, the outputs of which are stored in the databases 718. For example, seismic sensors of the field operations 710 can be used to perform a seismic survey to map subterranean features, such as facies and faults. In performing a seismic survey, seismic sources (e.g., seismic vibrators or explosions) generate seismic waves that propagate in the earth and seismic receivers (e.g., geophones) measure reflections generated as the seismic waves interact with boundaries between layers of a subsurface formation. The source and received signals are provided to the computational operations 712 where they are stored in the databases 718 and analyzed by the one or more computer systems 720.

In some implementations, one or more outputs 722 generated by the one or more computer systems 720 can be provided as feedback/input to the field operations 710 (either as direct input or stored in the databases 718). The field operations 710 can use the feedback/input to control physical components used to perform the field operations 710 in the real world.

For example, the computational operations 712 can process the seismic data to generate three-dimensional (3D) maps of the subsurface formation. The computational operations 712 can use these 3D maps to provide plans for locating and drilling exploratory wells. In some operations, the exploratory wells are drilled using logging-while-drilling (LWD) techniques which incorporate logging tools into the drill string. LWD techniques can enable the computational operations 712 to process new information about the formation and control the drilling to adjust to the observed conditions in real-time.

The one or more computer systems 720 can update the 3D maps of the subsurface formation as information from one exploration well is received and the computational operations 712 can adjust the location of the next exploration well based on the updated 3D maps. Similarly, the data received from production operations can be used by the computational operations 712 to control components of the production operations. For example, production well and pipeline data can be analyzed to predict slugging in pipelines leading to a refinery and the computational operations 712 can control machine operated valves upstream of the refinery to reduce the likelihood of plant disruptions that run the risk of taking the plant offline.

In some implementations of the computational operations 712, customized user interfaces can present intermediate or final results of the above-described processes to a user. Information can be presented in one or more textual, tabular, or graphical formats, such as through a dashboard. The information can be presented at one or more on-site locations (such as at an oil well or other facility), on the Internet (such as on a webpage), on a mobile application (or app), or at a central processing facility.

The presented information can include feedback, such as changes in parameters or processing inputs, that the user can select to improve a production environment, such as in the exploration, production, and/or testing of petrochemical processes or facilities. For example, the feedback can include parameters that, when selected by the user, can cause a change to, or an improvement in, drilling parameters (including drill bit speed and direction) or overall production of a gas or oil well. The feedback, when implemented by the user, can improve the speed and accuracy of calculations, streamline processes, improve models, and solve problems related to efficiency, performance, safety, reliability, costs, downtime, and the need for human interaction.

In some implementations, the feedback can be implemented in real-time, such as to provide an immediate or near-immediate change in operations or in a model. The term real-time (or similar terms as understood by one of ordinary skill in the art) means that an action and a response are temporally proximate such that an individual perceives the action and the response occurring substantially simultaneously. For example, the time difference for a response to display (or for an initiation of a display) of data following the individual's action to access the data can be less than 1 millisecond (ms), less than 1 second(s), or less than 10 s. While the requested data need not be displayed (or initiated for display) instantaneously, it is displayed (or initiated for display) without any intentional delay, accounting for processing limitations of a described computing system and time required to, for example, gather, accurately measure, analyze, process, store, or transmit the data.

Events can include readings or measurements captured by downhole equipment such as sensors, pumps, bottom hole assemblies, or other equipment. The readings or measurements can be analyzed at the surface, such as by using applications that can include modeling applications and machine learning. The analysis can be used to generate changes to settings of downhole equipment, such as drilling equipment. In some implementations, values of parameters or other variables that are determined can be used automatically (such as through using rules) to implement changes in oil or gas well exploration, production/drilling, or testing. For example, outputs of the present disclosure can be used as inputs to other equipment and/or systems at a facility. This can be especially useful for systems or various pieces of equipment that are located several meters or several miles apart or are in different countries or other jurisdictions.

Figure 8:
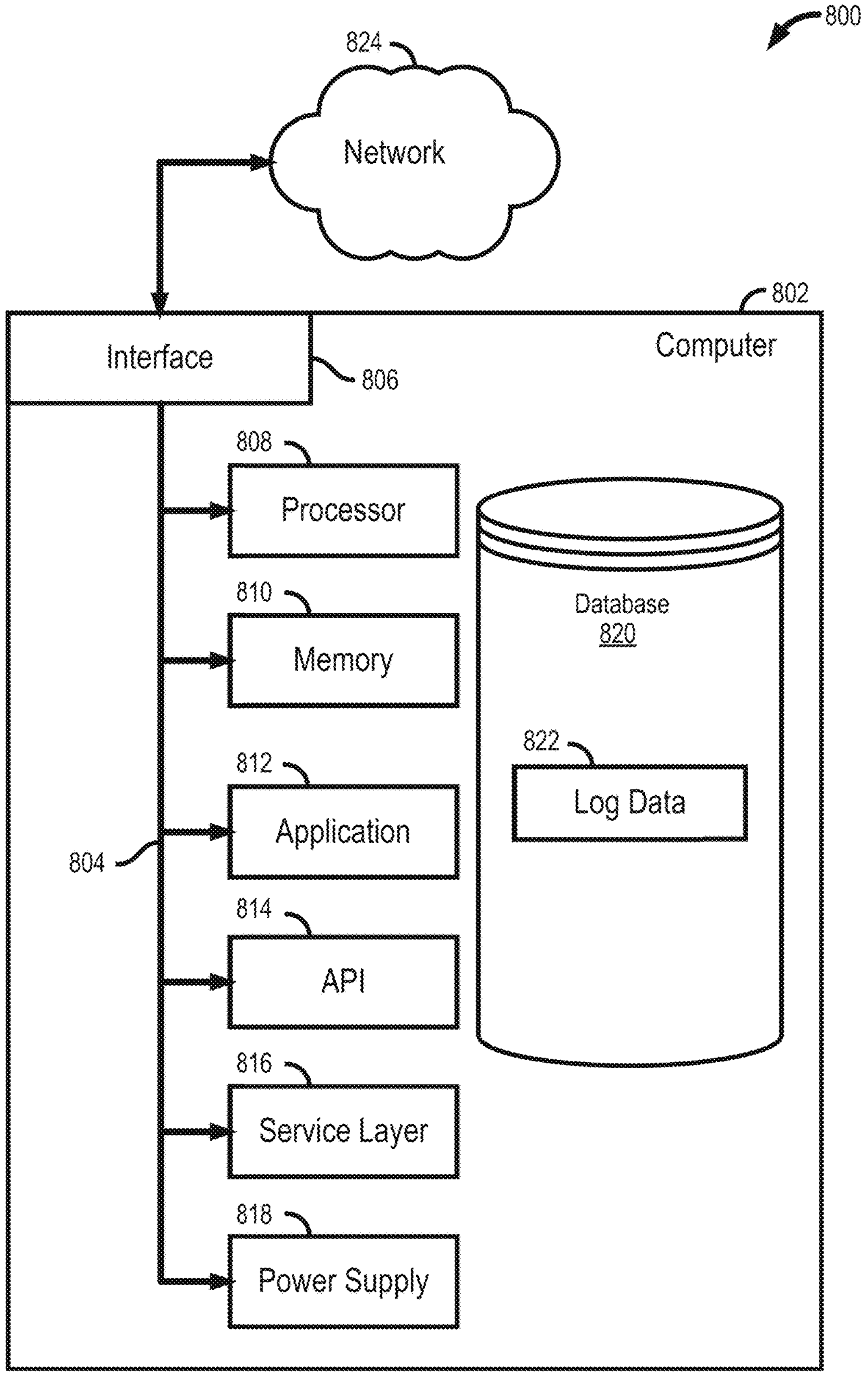
FIG. 8 is a diagram of an example computing system.

FIG. 8 is a block diagram of an example computer system 800 used to provide computational functionalities associated with described algorithms, methods, functions, processes, flows, and procedures described in the present disclosure, according to some implementations of the present disclosure. The illustrated computer 802 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 802 can include input devices such as keypads, keyboards, and touch screens that can accept user information. Also, the computer 802 can include output devices that can convey information associated with the operation of the computer 802. The information can include digital data, visual data, audio information, or a combination of information. The information can be presented in a graphical user interface (UI) (or GUI).

The computer 802 can serve in a role as a client, a network component, a server, a database, a persistency, or components of a computer system for performing the subject matter described in the present disclosure. The illustrated computer 802 is communicably coupled with a network 824. In some implementations, one or more components of the computer 802 can be configured to operate within different environments, including cloud-computing-based environments, local environments, global environments, and combinations of environments.

At a high level, the computer 802 is an electronic computing device operable to receive, transmit, process, store, and manage data and information associated with the described subject matter. According to some implementations, the computer 802 can also include, or be communicably coupled with, an application server, an email server, a web server, a caching server, a streaming data server, or a combination of servers.

The computer 802 can receive requests over network 824 from a client application (for example, executing on another computer 802). The computer 802 can respond to the received requests by processing the received requests using software applications. Requests can also be sent to the computer 802 from internal users (for example, from a command console), external (or third) parties, automated applications, entities, individuals, systems, and computers.

Each of the components of the computer 802 can communicate using a system bus 804. In some implementations, any or all of the components of the computer 802, including hardware or software components, can interface with each other or the interface 806 (or a combination of both), over the system bus 804. Interfaces can use an application programming interface (API) 814, a service layer 816, or a combination of the API 814 and service layer 816. The API 814 can include specifications for routines, data structures, and object classes. The API 814 can be either computer-language independent or dependent. The API 814 can refer to a complete interface, a single function, or a set of APIs.

The service layer 816 can provide software services to the computer 802 and other components (whether illustrated or not) that are communicably coupled to the computer 802. The functionality of the computer 802 can be accessible for all service consumers using this service layer. Software services, such as those provided by the service layer 816, can provide reusable, defined functionalities through a defined interface. For example, the interface can be software written in JAVA, C++, or a language providing data in extensible markup language (XML) format. While illustrated as an integrated component of the computer 802, in alternative implementations, the API 814 or the service layer 816 can be stand-alone components in relation to other components of the computer 802 and other components communicably coupled to the computer 802. Moreover, any or all parts of the API 814 or the service layer 816 can be implemented as child or sub-modules of another software module, enterprise application, or hardware module without departing from the scope of the present disclosure.

The computer 802 includes an interface 806. Although illustrated as a single interface 806 in FIG. 8, two or more interfaces 806 can be used according to implementations of the computer 802 and the described functionality. The interface 806 can be used by the computer 802 for communicating with other systems that are connected to the network 824 (whether illustrated or not) in a distributed environment. Generally, the interface 806 can include, or be implemented using, logic encoded in software or hardware (or a combination of software and hardware) operable to communicate with the network 824. More specifically, the interface 806 can include software supporting one or more communication protocols associated with communications. As such, the network 824 or the interface's hardware can be operable to communicate physical signals within and outside of the illustrated computer 802.

The computer 802 includes a processor 808. Although illustrated as a single processor 808 in FIG. 8, two or more processors 808 can be used according to implementations of the computer 802 and the described functionality. Generally, the processor 808 can execute instructions and can manipulate data to perform the operations of the computer 802, including operations using algorithms, methods, functions, processes, flows, and procedures as described in the present disclosure.

The computer 802 also includes a database 820 that can hold data (such as log data 822) for the computer 802 and other components connected to the network 824 (whether illustrated or not). For example, database 820 can be in-memory or a database storing data consistent with the present disclosure. In some implementations, database 820 can be a combination of two or more different database types (for example, hybrid in-memory and conventional databases) according to implementations of the computer 802 and the described functionality. Although illustrated as a single database 820 in FIG. 8, two or more databases (of the same, different, or combination of types) can be used according to implementations of the computer 802 and the described functionality. While database 820 is illustrated as an internal component of the computer 802, in alternative implementations, database 820 can be external to the computer 802.

The computer 802 also includes a memory 810 that can hold data for the computer 802 or a combination of components connected to the network 824 (whether illustrated or not). Memory 810 can store any data consistent with the present disclosure. In some implementations, memory 810 can be a combination of two or more different types of memory (for example, a combination of semiconductor and magnetic storage) according to implementations of the computer 802 and the described functionality. Although illustrated as a single memory 810 in FIG. 8, two or more memories 810 (of the same, different, or combination of types) can be used according to implementations of the computer 802 and the described functionality. While memory 810 is illustrated as an internal component of the computer 802, in alternative implementations, memory 810 can be external to the computer 802.

The application 812 can be an algorithmic software engine providing functionality according to implementations of the computer 802 and the described functionality. For example, application 812 can serve as one or more components, modules, or applications. Further, although illustrated as a single application 812, the application 812 can be implemented as multiple applications on the computer 802. In addition, although illustrated as internal to the computer 802, in alternative implementations, the application 812 can be external to the computer 802.

The computer 802 can also include a power supply 818. The power supply 818 can include a rechargeable or non-rechargeable battery that can be configured to be either user- or non-user-replaceable. In some implementations, the power supply 818 can include power-conversion and management circuits, including recharging, standby, and power management functionalities. In some implementations, the power-supply 818 can include a power plug to allow the computer 802 to be plugged into a wall socket or a power source to, for example, power the computer 802 or recharge a rechargeable battery.

There can be any number of computers 802 associated with, or external to, a computer system including the computer 802, with each computer 802 communicating over network 824. Further, the terms "client," "user," and other appropriate terminology can be used interchangeably, as appropriate, without departing from the scope of the present disclosure. Moreover, the present disclosure contemplates that many users can use one computer 802 and one user can use multiple computers 802.

Several implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

Several embodiments have been described. Nevertheless, it will be understood that various modifications may be made without departing from the scope of the data processing system described herein. Accordingly, other embodiments are within the scope of the following claims.

What is claimed is:

1. A method for determining a diagenesis level in a reservoir for performing hydrocarbon extraction, the method comprising:

receiving a set of open hole (OH) log data from one or more wells in the reservoir, the OH log data representing a subsurface of the reservoir;

executing a diagenesis model to process the set of OH log data, the diagenesis model being trained by thin-section image data that are correlated to labeled OH log data, the labeling identifying values for a quartz overgrowth rate (QOR), a clay coating rate (CCR), or a thin-section porosity in the subsurface based on a value in the OH log data and a type of the OH log;

determining, based on the executing, a prediction of a porosity of the reservoir, a permeability of the reservoir, or both the porosity and the permeability; and generating, based on the predicted porosity, a control signal representing a recommendation to drill a well at a location in the reservoir.

2. The method of claim 1, further comprising:

based on the predicted diagenesis level in the reservoir, generating a control signal configured for causing drilling of a well in the reservoir corresponding to a location a higher values of QOR, CCR, or VP relative to another location in the reservoir.

3. The method of claim 1, wherein the diagenesis model is trained by performing operations comprising:

obtaining image data from an imaging device, the image data representing at least a portion of a subsurface of the reservoir;

obtaining at least one thin-section image from the image data;

segmenting the thin-section image into a set of segments, each segment of the set including at least one grain;

extracting, from a segment of the set, first data representing a first ratio of quartz overgrowth particles to total particles;

extracting, from the segment of the set, second data representing a second ratio of a clay coated perimeter value to a total perimeter value; and training the diagenesis model based on the first ratio and the second ratio to predict the diagenesis level in the subsurface of the reservoir.

4. The method of claim 3, further comprising determining a visual porosity value for the portion of the subsurface of the reservoir by:

extracting region color data from the segment of the set;

filtering the segment of the set to remove blue color data from the segment;

extracting a region size data from the segment of the set based on the filtering;

determining a region size distribution based on the region size data; and determining a third ratio of visual porosity area to a total area, wherein the third ratio represents a thin-section porosity value, and wherein a reservoir quality is based on the thin-section porosity value.

5. The method of claim 1, wherein the OH log data comprises one or more of a thorium concentration log, a potassium concentration log, a shear slowness log, and a photoelectric absorption properties log.

6. The method of claim 1, wherein the OH log data comprises one or more of a thorium concentration log, a potassium concentration log, a sonic shear slowness log, a sonic compressional slowness log, and/or a density log.

7. The method of claim 1, wherein the OH log data comprises one or more of a sonic shear slowness log, a sonic compressional slowness log, a nuclear magnetic resonance (NMR) log, a dielectric log, and a density log.

8. A system for determining a diagenesis level in a reservoir for performing hydrocarbon extraction, the system comprising:

at least one processor; and a memory storing instructions, that, when executed by the at least one processor, cause the at least one processor to perform operations comprising:

receiving a set of open hole (OH) log data from one or more wells in the reservoir, the OH log data representing a subsurface of the reservoir;

executing a diagenesis model to process the set of OH log data, the diagenesis model being trained by thin-section image data that are correlated to labeled OH log data, the labeling identifying values for a quartz overgrowth rate (QOR), a clay coating rate (CCR), or a thin-section porosity in the subsurface based on a value in the OH log data and a type of the OH log;

determining, based on the executing, a prediction of a porosity of the reservoir, a permeability of the reservoir, or both the porosity and the permeability; and generating, based on the predicted porosity, a control signal representing a recommendation to drill a well at a location in the reservoir.

9. The system of claim 8, the operations further comprising:

based on the predicted diagenesis level in the reservoir, generating a control signal configured for causing drilling of a well in the reservoir corresponding to a location a higher values of QOR, CCR, or VP relative to another location in the reservoir.

10. The system of claim 8, wherein the diagenesis model is trained by performing operations comprising:

obtaining image data from an imaging device, the image data representing at least a portion of a subsurface of the reservoir;

obtaining at least one thin-section image from the image data;

segmenting the thin-section image into a set of segments, each segment of the set including at least one grain;

extracting, from a segment of the set, first data representing a first ratio of quartz overgrowth particles to total particles;

extracting, from the segment of the set, second data representing a second ratio of a clay coated perimeter value to a total perimeter value; and training the diagenesis model based on the first ratio and the second ratio to predict the diagenesis level in the subsurface of the reservoir.

11. The system of claim 10, the operations further comprising determining a visual porosity value for the portion of the subsurface of the reservoir by:

extracting region color data from the segment of the set;

filtering the segment of the set to remove blue color data from the segment;

extracting a region size data from the segment of the set based on the filtering;

determining a region size distribution based on the region size data; and determining a third ratio of visual porosity area to a total area, wherein the third ratio represents a thin-section porosity value, and wherein a reservoir quality is based on the thin-section porosity value.

12. The system of claim 8, wherein the OH log data comprises one or more of a thorium concentration log, a potassium concentration log, a shear slowness log, and a photoelectric absorption properties log.

13. The system of claim 8, wherein the OH log data comprises one or more of a thorium concentration log, a potassium concentration log, a sonic shear slowness log, a sonic compressional slowness log, and/or a density log.

14. The system of claim 8, wherein the OH log data comprises one or more of a sonic shear slowness log, a sonic compressional slowness log, a nuclear magnetic resonance (NMR) log, a dielectric log, and a density log.

15. One or more non-transitory computer readable media storing instructions for determining a diagenesis level in a reservoir for performing hydrocarbon extraction, the instructions, when executed by at least one processor, configured to cause the at least one processor to perform operations comprising:

receiving a set of open hole (OH) log data from one or more wells in the reservoir, the OH log data representing a subsurface of the reservoir;

executing a diagenesis model to process the set of OH log data, the diagenesis model being trained by thin-section image data that are correlated to labeled OH log data, the labeling identifying values for a quartz overgrowth rate (QOR), a clay coating rate (CCR), or a thin-section porosity in the subsurface based on a value in the OH log data and a type of the OH log;

determining, based on the executing, a prediction of a porosity of the reservoir, a permeability of the reservoir, or both the porosity and the permeability; and generating, based on the predicted porosity, a control signal representing a recommendation to drill a well at a location in the reservoir.

16. The one or more non-transitory computer readable media of claim 15, the operations further comprising:

based on the predicted diagenesis level in the reservoir, generating a control signal configured for causing drilling of a well in the reservoir corresponding to a location a higher values of QOR, CCR, or VP relative to another location in the reservoir.

17. The one or more non-transitory computer readable media of claim 15, wherein the diagenesis model is trained by performing operations comprising:

obtaining image data from an imaging device, the image data representing at least a portion of a subsurface of the reservoir;

obtaining at least one thin-section image from the image data;

segmenting the thin-section image into a set of segments, each segment of the set including at least one grain;

extracting, from a segment of the set, first data representing a first ratio of quartz overgrowth particles to total particles;

extracting, from the segment of the set, second data representing a second ratio of a clay coated perimeter value to a total perimeter value; and training the diagenesis model based on the first ratio and the second ratio to predict the diagenesis level in the subsurface of the reservoir.

18. The one or more non-transitory computer readable media of claim 17, the operations further comprising determining a visual porosity value for the portion of the subsurface of the reservoir by:

extracting region color data from the segment of the set;

filtering the segment of the set to remove blue color data from the segment;

extracting a region size data from the segment of the set based on the filtering;

determining a region size distribution based on the region size data; and determining a third ratio of visual porosity area to a total area, wherein the third ratio represents a thin-section porosity value, and wherein a reservoir quality is based on the thin-section porosity value.

19. The one or more non-transitory computer readable media of claim 15, wherein the OH log data comprises one or more of a thorium concentration log, a potassium concentration log, a shear slowness log, and a photoelectric absorption properties log.

20. The one or more non-transitory computer readable media of claim 15, wherein the OH log data comprises one or more of a thorium concentration log, a potassium concentration log, a sonic shear slowness log, a sonic compressional slowness log, and/or a density log.

* * * * *